United States Patent
Foley et al.

(10) Patent No.: US 11,213,404 B2
(45) Date of Patent: *Jan. 4, 2022

(54) EXPANDING INTERBODY IMPLANT AND ARTICULATING INSERTER AND METHODS OF USE

(71) Applicant: WARSAW ORTHOPEDIC, INC., Warsaw, IN (US)

(72) Inventors: Kevin T. Foley, Germantown, TN (US); Roy K. Lim, Germantown, TN (US); Matthew M. Morrison, Cordova, TN (US); Jonathan M. Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 200 days.

This patent is subject to a terminal disclaimer.

(21) Appl. No.: 16/587,572

(22) Filed: Sep. 30, 2019

(65) Prior Publication Data
US 2020/0038200 A1   Feb. 6, 2020

Related U.S. Application Data

(63) Continuation of application No. 15/480,718, filed on Apr. 6, 2017, now Pat. No. 10,470,894.

(51) Int. Cl.
*A61F 2/44* (2006.01)
*A61F 2/30* (2006.01)

(52) U.S. Cl.
CPC ............ *A61F 2/4465* (2013.01); *A61F 2/447* (2013.01); *A61F 2002/30525* (2013.01);
(Continued)

(58) Field of Classification Search
CPC .......... A61F 2/44; A61F 2/4455; A61F 2/446; A61F 2/4465; A61F 2/447; A61F 2002/4475
See application file for complete search history.

(56) References Cited

U.S. PATENT DOCUMENTS

| 4,743,256 A | 5/1988 | Brantigan |
| 4,834,757 A | 5/1989 | Brantigan |

(Continued)

FOREIGN PATENT DOCUMENTS

| CN | 105025846 A | 11/2015 |
| CN | 205107983 U | 3/2016 |

(Continued)

OTHER PUBLICATIONS

European Search Report completed Aug. 16, 2018 issued in EP 18159715.4 (filing date Mar. 2, 2018), 8 pages.
(Continued)

*Primary Examiner* — Eric S Gibson
(74) *Attorney, Agent, or Firm* — Sorell, Lenna & Schmidt, LLP

(57) ABSTRACT

A device includes a first endplate having an engagement surface and first and second extensions. The first extension has a first ramp and the second extension has a first slot. A second endplate includes a second engagement surface and third and fourth extensions. The third extension has a second ramp and the fourth extension has a second slot. A wedge is positioned between the endplates and includes a first inclined portion that engages the first ramp and a second inclined portion that engages the second ramp. The wedge has first and second apertures. A first pin extends through the first aperture and the first slot. A second pin extends through the second aperture and the second slot. The wedge is movable relative to the endplates to move the device from a first height to an increased second height. Methods of use are disclosed.

20 Claims, 12 Drawing Sheets

(52) U.S. Cl.
CPC ............. *A61F 2002/30556* (2013.01); *A61F 2002/30593* (2013.01); *A61F 2002/443* (2013.01)

(56) References Cited

U.S. PATENT DOCUMENTS

| | | | |
|---|---|---|---|
| 4,863,476 A | 9/1989 | Shepperd | |
| 4,878,915 A | 11/1989 | Brantigan | |
| 5,171,278 A | 12/1992 | Pisharodi | |
| 5,192,327 A | 3/1993 | Brantigan | |
| 5,425,772 A | 6/1995 | Brantigan | |
| 5,443,514 A | 8/1995 | Steffee | |
| 5,484,437 A | 1/1996 | Michelson | |
| 5,505,732 A | 4/1996 | Michelson | |
| 5,554,191 A | 9/1996 | Lahille et al. | |
| D377,096 S | 12/1996 | Michelson | |
| 5,609,635 A | 3/1997 | Michelson | |
| 5,653,763 A | 8/1997 | Errico et al. | |
| 5,658,335 A | 8/1997 | Allen | |
| 5,665,122 A | 9/1997 | Kambin | |
| 5,716,415 A | 2/1998 | Steffee | |
| 5,755,732 A | 5/1998 | Green et al. | |
| 5,766,252 A | 6/1998 | Henry et al. | |
| 5,782,830 A | 6/1998 | Farris | |
| 5,776,199 A | 7/1998 | Michelson | |
| 5,865,848 A | 2/1999 | Baker | |
| 5,888,224 A | 3/1999 | Beckers | |
| 5,888,227 A | 3/1999 | Cottle | |
| 5,893,889 A | 4/1999 | Harrington | |
| 5,895,426 A | 4/1999 | Scarborough et al. | |
| 5,980,522 A | 11/1999 | Koros et al. | |
| 5,984,922 A | 11/1999 | Mckay | |
| 6,045,579 A | 4/2000 | Hochschuler et al. | |
| 6,080,158 A | 6/2000 | Lin | |
| 6,080,193 A | 6/2000 | Hochschuler et al. | |
| 6,090,143 A | 7/2000 | Meriweather et al. | |
| 6,102,950 A | 8/2000 | Vaccaro | |
| 6,113,638 A | 9/2000 | Williams | |
| 6,117,174 A | 9/2000 | Nolan | |
| 6,159,245 A | 12/2000 | Meriweather et al. | |
| 6,176,881 B1 | 1/2001 | Shar et al. | |
| 6,176,882 B1* | 1/2001 | Biedermann | A61F 2/447 623/17.15 |
| 6,183,517 B1 | 2/2001 | Suddaby | |
| 6,190,414 B1 | 2/2001 | Young et al. | |
| 6,217,579 B1 | 4/2001 | Koros | |
| 6,245,108 B1 | 6/2001 | Biscup | |
| 6,319,257 B1 | 11/2001 | Carignan et al. | |
| 6,368,351 B1 | 4/2002 | Glenn et al. | |
| 6,371,989 B1 | 4/2002 | Chauvin et al. | |
| 6,419,705 B1 | 7/2002 | Erickson | |
| 6,419,706 B1 | 7/2002 | Graf | |
| 6,432,108 B1 | 8/2002 | Burgess et al. | |
| 6,436,140 B1 | 8/2002 | Liu et al. | |
| 6,436,142 B1 | 8/2002 | Paes et al. | |
| 6,443,989 B1 | 9/2002 | Jackson | |
| 6,454,806 B1 | 9/2002 | Cohen et al. | |
| 6,454,807 B1 | 9/2002 | Jackson | |
| 6,468,276 B1 | 10/2002 | McKay | |
| 6,517,051 B1 | 2/2003 | Cavanaugh | |
| 6,562,074 B2 | 5/2003 | Gerbec et al. | |
| 6,576,016 B1 | 6/2003 | Hochschuler et al. | |
| 6,641,614 B1 | 11/2003 | Wagner et al. | |
| 6,648,917 B2 | 11/2003 | Gerbec et al. | |
| 6,676,703 B2 | 1/2004 | Biscup | |
| 6,685,742 B1 | 2/2004 | Jackson | |
| 6,706,070 B1 | 3/2004 | Wagner et al. | |
| 6,767,366 B2 | 7/2004 | Lee et al. | |
| 6,830,589 B2 | 12/2004 | Erickson | |
| 6,835,206 B2 | 12/2004 | jackson | |
| 6,852,129 B2 | 2/2005 | Gerbec et al. | |
| 6,863,673 B2 | 3/2005 | Gerbec et al. | |
| 6,893,464 B2 | 5/2005 | Kiester | |
| 7,204,853 B2 | 4/2007 | Gordon et al. | |
| 7,211,112 B2 | 5/2007 | Baynham et al. | |
| 7,217,293 B2 | 5/2007 | Branch, Jr. | |
| 7,316,714 B2 | 1/2008 | Gordon et al. | |
| 7,569,074 B2 | 8/2009 | Eisermann et al. | |
| 7,594,932 B2 | 9/2009 | Aferzon et al. | |
| 7,744,649 B2 | 6/2010 | Moore | |
| 7,749,270 B2 | 7/2010 | Peterman | |
| 7,753,958 B2 | 7/2010 | Gordon et al. | |
| 7,828,849 B2* | 11/2010 | Lim | A61F 2/4465 623/17.16 |
| 7,850,733 B2 | 12/2010 | Baynham et al. | |
| 7,875,078 B2 | 1/2011 | Wysocki et al. | |
| 7,909,869 B2 | 3/2011 | Gordon et al. | |
| 8,062,375 B2* | 11/2011 | Glerum | A61F 2/4611 623/17.16 |
| 8,105,382 B2 | 1/2012 | Olmos et al. | |
| 8,123,810 B2 | 2/2012 | Gordon et al. | |
| 8,133,232 B2 | 3/2012 | Levy et al. | |
| 9,271,846 B2* | 3/2016 | Lim | A61F 2/4611 |
| 9,750,617 B2* | 9/2017 | Lim | A61B 17/025 |
| 9,801,734 B1* | 10/2017 | Stein | A61F 2/447 |
| 10,111,755 B2* | 10/2018 | Foley | A61F 2/4465 |
| 10,265,191 B2* | 4/2019 | Lim | A61B 17/025 |
| 10,470,894 B2* | 11/2019 | Foley | A61F 2/4465 |
| 2001/0032020 A1 | 10/2001 | Besselink | |
| 2002/0045943 A1 | 4/2002 | Uk | |
| 2002/0045945 A1 | 4/2002 | Liu et al. | |
| 2002/0068976 A1 | 6/2002 | Jackson | |
| 2002/0068977 A1 | 6/2002 | Jackson | |
| 2002/0128713 A1 | 9/2002 | Ferree | |
| 2002/0128716 A1 | 9/2002 | Cohen et al. | |
| 2002/0138146 A1 | 9/2002 | Jackson | |
| 2002/0143401 A1 | 10/2002 | Michelson | |
| 2002/0177897 A1 | 11/2002 | Michelson | |
| 2003/0130739 A1 | 7/2003 | Gerbec et al. | |
| 2003/0139812 A1 | 7/2003 | Garcia et al. | |
| 2003/0149484 A1 | 8/2003 | Michelson | |
| 2004/0059421 A1 | 3/2004 | Glenn et al. | |
| 2004/0087947 A1* | 5/2004 | Lim | A61F 2/447 606/247 |
| 2004/0102847 A1 | 5/2004 | Sato et al. | |
| 2004/0127993 A1 | 7/2004 | Kast et al. | |
| 2004/0127994 A1 | 7/2004 | Kast et al. | |
| 2005/0278026 A1 | 12/2005 | Gordon et al. | |
| 2006/0247770 A1 | 11/2006 | Peterman | |
| 2007/0270968 A1 | 11/2007 | Baynham et al. | |
| 2008/0147193 A1* | 6/2008 | Matthis | A61F 2/4425 623/17.16 |
| 2009/0222100 A1 | 9/2009 | Cipoletti et al. | |
| 2010/0286779 A1* | 11/2010 | Thibodeau | A61F 2/4611 623/17.11 |
| 2010/0292796 A1* | 11/2010 | Greenhalgh | A61B 17/8858 623/17.11 |
| 2011/0172774 A1 | 7/2011 | Varela | |
| 2013/0023994 A1* | 1/2013 | Glerum | A61F 2/4611 623/17.16 |
| 2014/0121774 A1* | 5/2014 | Glerum | A61F 2/447 623/17.16 |
| 2014/0249632 A1* | 9/2014 | Weiman | A61F 2/4425 623/17.16 |
| 2015/0150691 A1* | 6/2015 | Lim | A61F 2/4611 623/17.15 |
| 2017/0014240 A1* | 1/2017 | Seifert | A61F 2/447 |
| 2017/0296353 A1* | 10/2017 | Matthis | A61F 2/4465 |
| 2018/0042732 A1* | 2/2018 | Seifert | A61F 2/4455 |
| 2018/0289505 A1* | 10/2018 | Foley | A61F 2/447 |
| 2020/0038200 A1* | 2/2020 | Foley | A61F 2/4455 |

FOREIGN PATENT DOCUMENTS

| | | |
|---|---|---|
| FR | 2824261 | 8/2002 |
| WO | 1999032054 A1 | 1/1997 |
| WO | 1997000054 A1 | 3/1997 |
| WO | 1998048738 A1 | 5/1998 |
| WO | 1999042062 A1 | 8/1999 |
| WO | 2000074605 A1 | 12/2000 |
| WO | 2016127139 | 8/2016 |

(56) References Cited

FOREIGN PATENT DOCUMENTS

WO          2016127139 A1    8/2016
WO     WO 2016127139 A1    8/2016

OTHER PUBLICATIONS

European Search Report for EP18159715.4 date of completion is Aug. 16, 2018 (8 pages).
China National Intellectual Property Administration (CNIPA) Notice of the 1st Office Action, Application No. 201810288162.8, dated May 6, 2021.
European Patent Office, Munich, Germany, European Search Report, Application No. 0198941.5-1132, dated Feb. 1, 2021.
China National Intellectual Property Administration (CNIPA) Notice of the 2nd Office Action, Application No. 201810238162.8, Date of Dispatch, dated Nov. 9, 2021.

* cited by examiner

EXPANDING INTERBODY IMPLANT AND ARTICULATING INSERTER AND METHODS OF USE

CROSS REFERENCE TO RELATED APPLICATIONS

This application is a continuation of U.S. patent application Ser. No. 15/480,718, filed on Apr. 6, 2017, which is hereby expressly incorporated herein by reference, in its entirety.

TECHNICAL FIELD

The present disclosure generally relates to medical devices, systems and methods for the treatment of musculoskeletal disorders, and more particularly to an expandable interbody implant system and method for treating a vertebral column.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. These treatments may employ interbody implants. This disclosure describes an improvement over these prior art technologies.

SUMMARY

Accordingly, an expandable interbody implant system and method are disclosed. In one embodiment, the system includes a device to space apart vertebral members. The device comprises a first endplate comprising a first engagement surface and first and second extensions that each extend away from the first engagement surface. The first extension comprises a first ramp and the second extension comprises a first slot. A second endplate comprises a second engagement surface and third and fourth extensions that each extend away from the second engagement surface. The third extension comprises a second ramp and the fourth extension comprises a second slot. A wedge is positioned between the endplates. The wedge comprises an upper surface having a first inclined portion that slidably engages the first ramp and a lower surface having a second inclined portion that slidably engages the second ramp. The wedge comprises first and second apertures. A first pin extends through the first aperture and the first slot. A second pin extends through the second aperture and the second slot. The wedge is movable relative to the endplates to move the device between a first configuration having a first height between the engagement surfaces and a second configuration having an increased second height between the engagement surfaces.

BRIEF DESCRIPTION OF THE DRAWINGS

The present disclosure will become more readily apparent from the specific description accompanied by the following drawings, in which.

DETAILED DESCRIPTION

Figure 1:
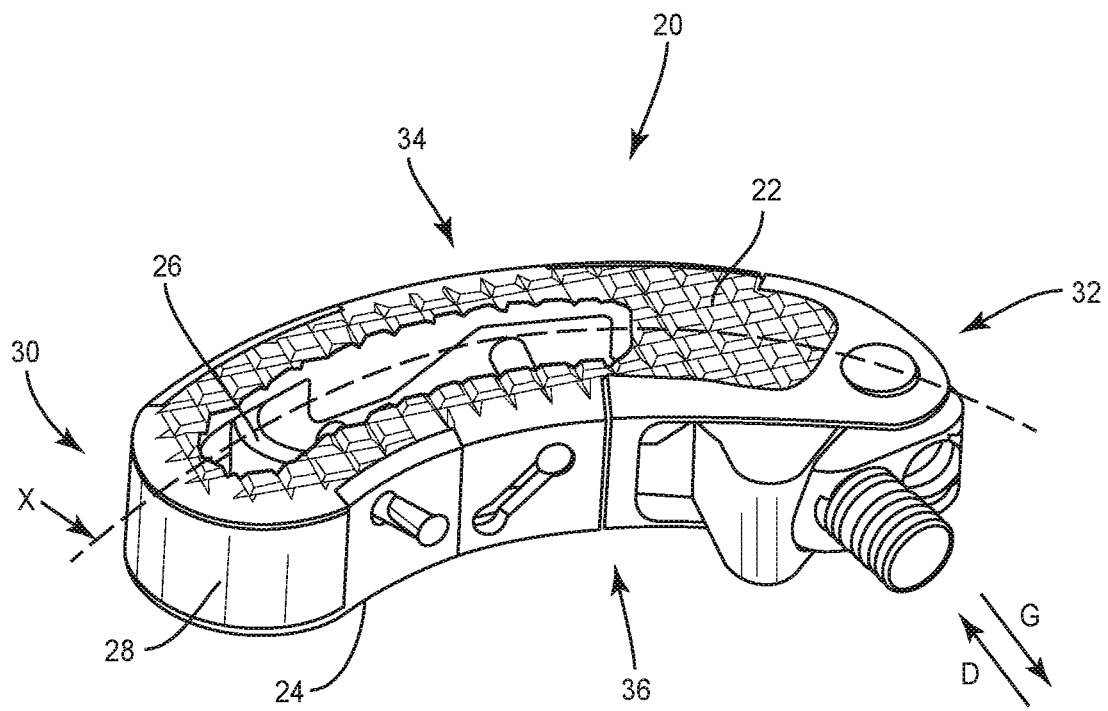
FIG. 1 is a perspective view of one embodiment of an implant of a system in accordance with the principles of the present disclosure.
Figure 2:
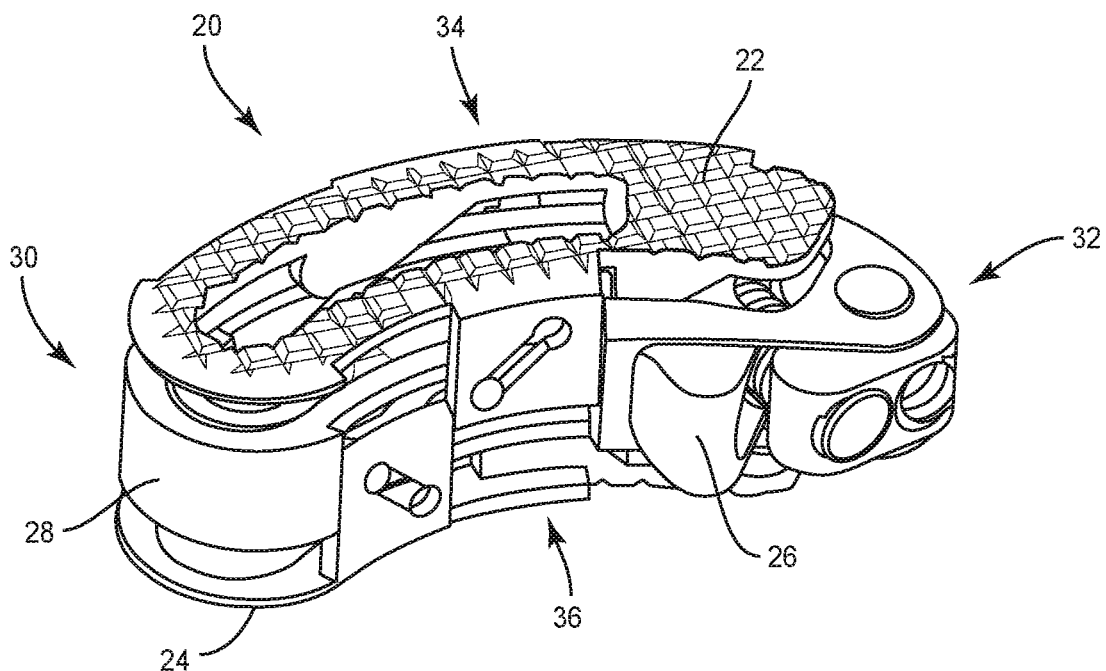
FIG. 2 is a perspective view of the implant shown in FIG. 1.

The exemplary embodiments of an expandable interbody implant system and related methods of use disclosed herein are discussed in terms of medical devices for the treatment of musculoskeletal disorders and more particularly, in terms of an expandable interbody implant system and related methods for treating a vertebral column. It is envisioned that the implant system may provide, for example, fusion, decompression, restoration of sagittal balance and resistance of subsidence into tissue, such as, for example, surfaces of vertebral endplates. It is further envisioned that the system includes an interbody implant that expands after insertion into an intervertebral disc space and has several features, such as, for example, facile insertion into the intervertebral disc space such that less bone removal is necessary during a surgical procedure, decompression of nerve roots, and expansion to restore sagittal balance such that more expansion is provided on an anterior side relative to a posterior side in for example, a lumbar application. In some embodiments, the interbody implant can be inserted into the intervertebral disc space using a passive (e.g., non-steerable) or active (e.g., steerable) inserter. In some embodiments, the interbody implant is configured to be inserted at about a 15 degree angle and can be articulated about 85 degrees to about 100 degrees. This arrangement allows for continuous angulation, which allows implant deployment at any angle from about 15 through about 85-100 degrees. That is, the interbody implant is configured to be inserted at a starting angle of about 15 degrees with about 85-100 degrees of additional angulation. In some embodiments, articulation is achieved through the use of a pivot that is secured to a frame of the implant. In some embodiments, the pivot is secured to the frame using pivot plugs. In some embodiments, the interbody implant can be deployed at any insertion angle. In some embodiments, the interbody implant can be deployed at any angle from about 15 to about 85-90 degrees. In some embodiments, the expandable interbody implant has a 32 millimeter (mm) by 13.5 mm footprint. In some embodiments, the expandable interbody implant has a maximum insertion footprint of about 13.5 mm at 15 degrees.

In some embodiments, the expandable interbody implant has an undeployed height and can be expanded to a deployed height. In some embodiments, the deployed height is less than twice the undeployed height. In some embodiments, the deployed height is twice the undeployed height. In some embodiments, the deployed height is greater than twice the undeployed height. In some embodiments, the expandable interbody implant has an undeployed height of about 7 mm and can be expanded to a deployed height of about 14 mm. In some embodiments, the expandable interbody implant has an undeployed height of about 8 mm and can be expanded to a deployed height of about 16 mm. In some embodiments, the expandable interbody implant has an undeployed height of about 9 mm and can be expanded to a deployed height of about 18 mm. In some embodiments, the expandable interbody implant has an undeployed height of about 10 mm and can be expanded to a deployed height of about 20 mm. In some embodiments, the expandable interbody implant is deployed using a drive screw to move the implant from the undeployed height to the deployed height. The drive screw threads into the pivot discussed herein. In some embodiments, the drive screw comprises a ball tip that is positioned in a circular or semi-circular trough in a wedge of the implant, wherein unscrewing the ball tipped screw retracts the wedge and undeploys the implant. In some embodiments, the expandable interbody implant may be incrementally deployed from the undeployed height to the deployed height.

In some embodiments, the expandable interbody implant includes implant endplates, such as, for example, upper and lower implant endplates each having ramps that engage ramps (inclined portions) of the wedge. That is, each of the implant endplates include multiple ramps. The wedge includes an upper surface with multiple ramps that engage the ramps of the upper endplate and a lower surface with multiple ramps that engage the ramps of the lower endplate. The wedge moves relative to the endplates to move the ramps of the endplates along the ramps of the wedge to move the implant from the undeployed height to the deployed height. As the wedge moves away from the pivot, endplate deployment is achieved. The ramps are staggered such that opposing ramps are not aligned or mirrored. The relative position of the implant endplates with respect to the pivot is maintained by the frame. In some embodiments, the ramps of the implant endplate reside on the ramps of the wedge when the implant is fully deployed. In some embodiments, the ramps have asymmetrical geometry to allow the endplates to be driven into a parallel relationship. In some embodiments, the ramps have asymmetrical geometry to allow the endplates to be driven into a non-parallel relationship (kyphosis or lordosis). In some embodiments, the ramps have asymmetrical geometry to allow the endplates to simultaneously correct sagittal and coronal imbalance while restoring interbody height.

In some embodiments, the expandable interbody implant is kidney shaped and defines a curve of radii X. The wedge travels along radii X as the implant moves between the undeployed and deployed heights. In some embodiments, all ramps, inclined portions, slots and other features converge to the center of radii X in order to function, while avoiding binding. In some embodiments, the radii can be infinity and the implant is a straight implant. In some embodiments, the expandable interbody implant is rectangular, bullet-shaped, lordotic or kyphotic-shaped.

In some embodiments, the expandable interbody implant system is employed with a posterior approach to the intervertebral disc space. In some embodiments, the expandable interbody implant has a titanium construction. In some embodiments, the expandable interbody implant is closable. In some embodiments, the expandable interbody implant has a thru design that defines a graft pocket configured for disposal of a bone graft, for example. In some embodiments, the expandable interbody implant has multiple windows for entry of graft material into a cage defined by the implant. In some embodiments, the expandable interbody implant has textured upper and lower surfaces for improved gripping of vertebral surfaces.

It is envisioned that the expandable interbody implant and methods of use disclosed herein can be employed to obtain fusion of vertebrae through a minimally invasive or percutaneous technique. In one embodiment, the disclosed expandable interbody implant and methods of use can provide improved spinal treatment with a device that is made to expand vertically to create lordosis in vertebrae. It is contemplated that the expandable interbody implant and methods of use disclosed herein provide a cavity of relatively large volume for post-packing of at least one agent, for example, bone graft.

It is also envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed expandable interbody implant may be alternatively employed in a surgical treatment with a patient in a prone or supine position, and/or employ various surgical approaches to the spine, including anterior, posterior, posterior mid-line, medial, lateral, postero-lateral, and/or antero-lateral approaches, and in other body regions. The expandable interbody implant of the present disclosure may also be alternatively employed with procedures for treating the lumbar, cervical, thoracic and pelvic regions of a spinal column. The expandable interbody implant and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, outer, inner, terminal (denoting position or location), left and right, posterior, anterior, and the like, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (for example, preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, for example, arresting its development, or relieving the disease, for example, causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of an expandable interbody implant and related methods of employing the expandable interbody implant in accordance with the principles of the present disclosure. Alternate embodiments are also disclosed. Reference will now be made in detail to the exemplary embodiments of the present disclosure, which are illustrated in the accompanying figures. Turning now to FIGS. 1-25, there are illustrated components of an interbody implant system including an intervertebral implant 20 in accordance with the principles of the present disclosure.

The components of the system can be fabricated from biologically acceptable materials suitable for medical applications, including metals, synthetic polymers, ceramics and bone material and/or their composites, depending on the particular application and/or preference of a medical practitioner. For example, the components of the system, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (for example, Nitinol, super elastoplastic metals, such as GUM METAL® manufactured by Toyota Material Incorporated of Japan), ceramics and composites thereof such as calcium phosphate (for example, SKELITE™ manufactured by Biologix Inc.), thermoplastics such as polyaryl ether ketone (PAEK) including polyether ether ketone (PEEK), polyether ketone ketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polylactide, polyglycolide, polytyrosine carbonate, polycaprolactone and their combinations. Various components of the system may be fabricated from material composites, including the above materials, to achieve various desired characteristics such as strength, rigidity, elasticity, flexibility, compliance, biomechanical performance, durability and radiolucency or imaging preference. The components of the system, individually or collectively, may also be fabricated from a heterogeneous material such as a combination of two or more of the above-described materials.

The system including intervertebral implant 20 can be employed as a stabilization device in fusion and fixation procedures, for example, for patients suffering from a spinal disorder to provide height restoration between vertebral bodies, decompression, restoration of sagittal balance and/or resistance of subsidence into vertebral endplates. The components of the interbody implant system may be monolithically formed, integrally connected or include fastening elements and/or instruments, for example, as described herein.

Figure 3:
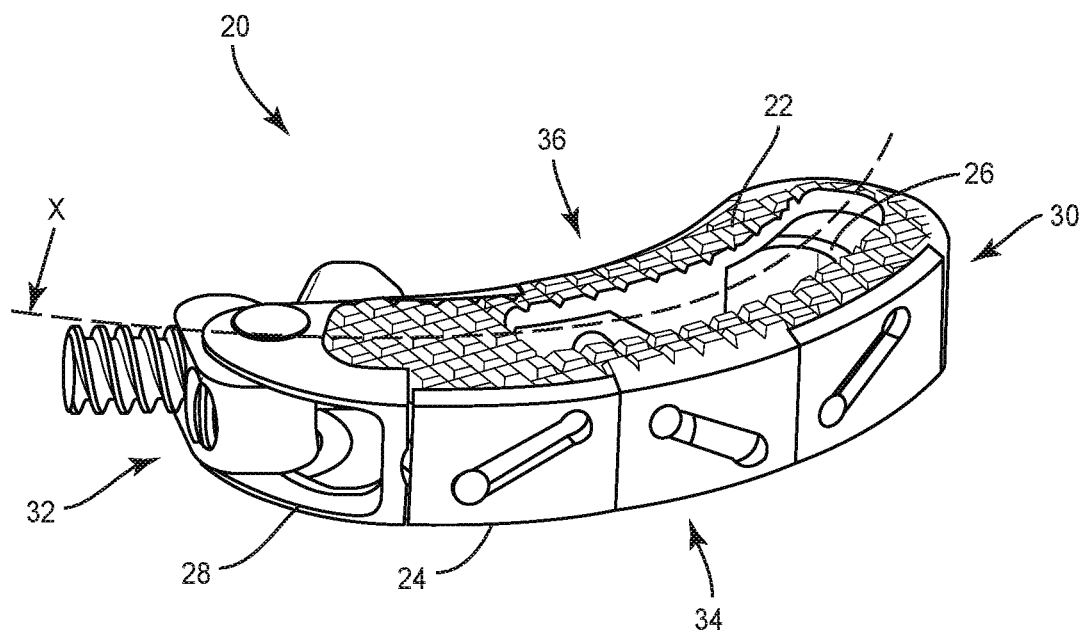
FIG. 3 is a perspective view of the implant shown in FIG. 1.
Figure 4:
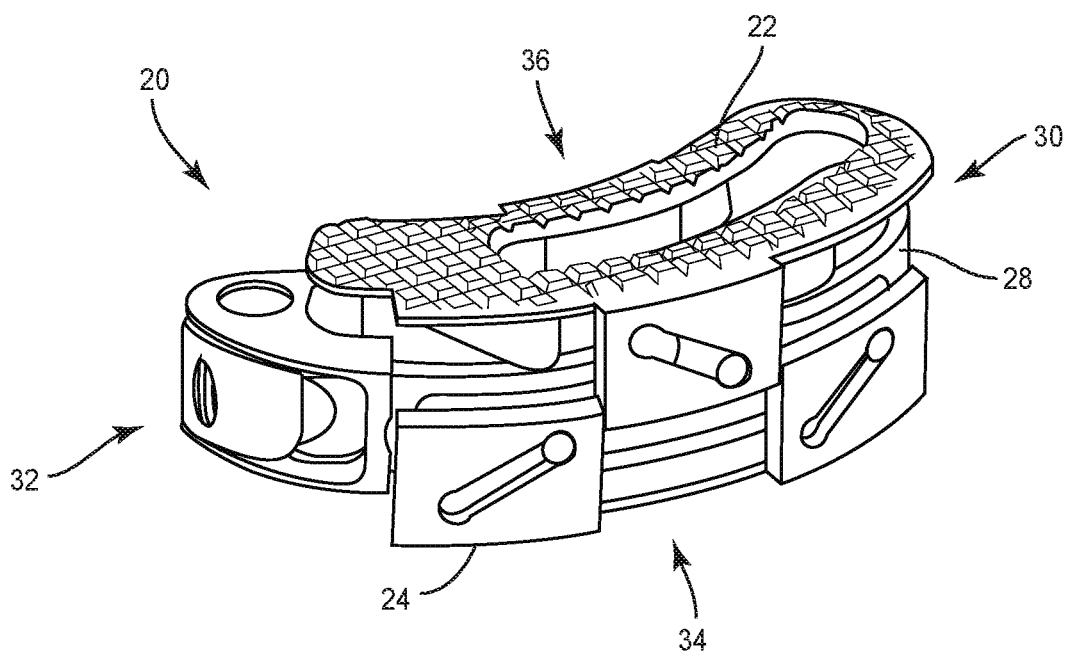
FIG. 4 is a perspective view of the implant shown in FIG. 1.

Intervertebral implant 20 comprises an endplate 22, an opposite endplate 24 and a wedge 26 positioned between endplates 22, 24. Wedge 26 and portions of endplates 22, 24 are positioned within a frame 28 of implant 20, as discussed herein. Wedge 26 is configured to translate relative to endplates 22, 24 to move implant 20 between an undeployed or unexpanded configuration, shown in FIGS. 1 and 3, and a deployed or expanded configuration, shown in FIGS. 2 and 4, In some embodiments, implant 20 is kidney-shaped and extends between an end 30 and an opposite end 32 along a radius, such as, for example an arc X, as shown in FIGS. 1 and 3. As such, a side 34 of implant 20 is convexly curved from end 30 to end 32 and an opposite side 36 of implant 20 is concavely curved from end 30 to end 32. In some embodiments, arc X has a continuous radius of curvature. In some embodiments, arc X has a variable radius of curvature. In some embodiments, implant 20 is square, rectangular, oval, bullet-shaped, lordotic or kyphotic-shaped. In some embodiments, implant 20 is made from one or more of the materials discussed herein. In some embodiments, implant 20 is made from a metal, such as, for example, titanium. In some embodiments, implant 20 consists of titanium or PEEK.

Figure 5:
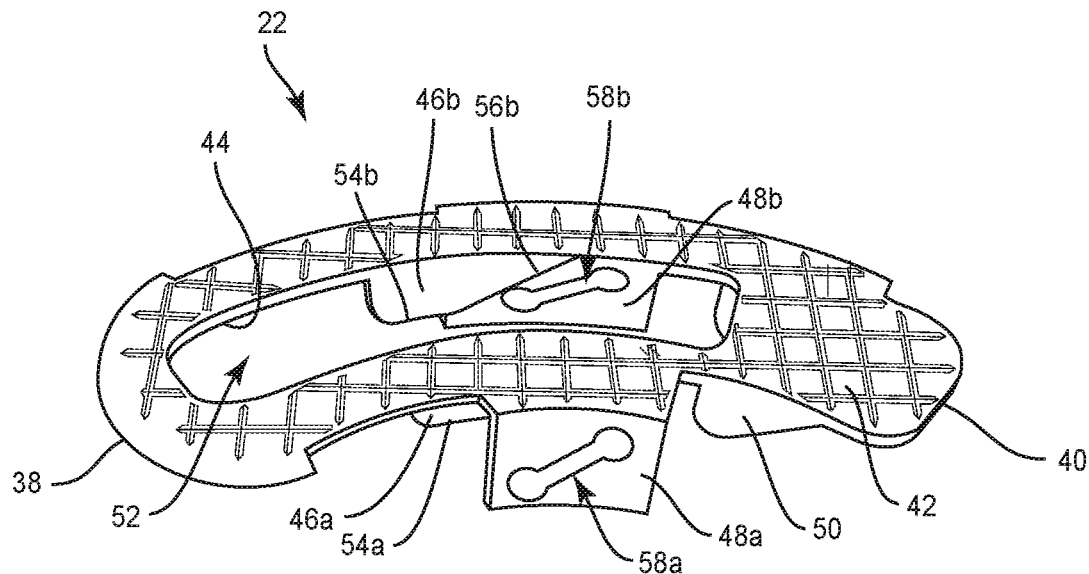
FIG. 5 is a top, perspective view of a component of the implant shown in FIG. 1.
Figure 6:
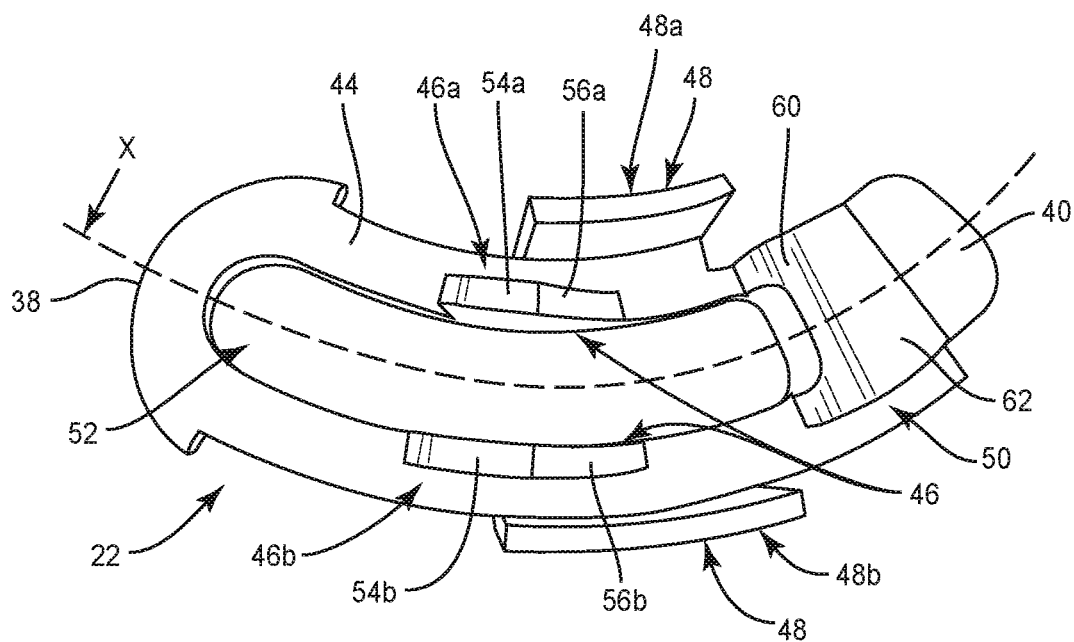
FIG. 6 is a bottom view of a component of the implant shown in FIG. 1.

Endplate 22 extends along arc X between an end 38 and an opposite end 40, as shown in FIGS. 5 and 6. End 38 is positioned adjacent to end 30 of implant 20 and end 40 is positioned adjacent to end 32 of implant 20, Endplate 22 is curved along arc X. As such, one side of endplate 22 is convexly curved between ends 38, 40 and an opposite side of endplate 22 is concavely curved between ends 38, 40. Endplate 22 comprises an engagement surface 42 configured to engage a first vertebra and an inner surface 44 opposite engagement surface 42. Inner surface 44 faces away from engagement surface 42. Endplate 22 comprises extensions 46, 48, 50 that extend from inner surface 44 such that extensions 46, 48, 50 each extend away from engagement surface 42. Extension 46 includes an extension 46a and an extension 46b that is spaced apart from extension 46a by an opening 52 that extends through engagement surface 42 and inner surface 44. Extension 48 includes an extension 48a and an extension 48b that is spaced apart from extension 48a such that extensions 46a, 46b are positioned between extensions 48a, 48b. Extension 50 extends across opening 52 from one side of endplate 22 to an opposite side of endplate 22.

Extension 46a includes a planar portion 54a and a ramp 56a that extends from planar portion 54a. Extension 46b includes a planar portion 54b and a ramp 56b that extends from planar portion 54b. Ramps 56a, 56b are configured to slidably engage inclined portions of wedge 26 to move implant 20 between the unexpanded configuration shown in FIGS. 1 and 3 and the expanded configuration shown in FIGS. 2 and 4, as discussed herein. In some embodiments, planar portion 54a extends parallel or substantially parallel to planar portion 54b. In some embodiments, planar portion 54a and planar portion 54b have the same pitch or a similar pitch, but different diameters such that planar portion 54b has a larger radius of curvature than planar portion 54a along arc X. As such, planar portion 54b has a length that is greater than that of planar portion 54a. In some embodiments, planar portions 54a, 54b each extend parallel to engagement surface 42 and ramps 56a, 56b each extend transverse to engagement surface 42. In some embodiments, ramps 56a, 56b extend at an acute angle relative to engagement surface 42. In that endplate 22 is curved along arc X, planar portion 54b has a maximum length that is greater than a maximum length of planar portion 54a and ramp 56b has a maximum length that is greater than a maximum length of ramp 56a. This allows engagement surface 42 to remain parallel to an engagement surface of endplate 24 as implant 20 moves between the unexpanded configuration and the expanded configuration, as discussed herein. In some embodiments, planar portion 54a, planar portion 54b, ramp 56a and/or ramp 56b may be disposed at alternate orientations, relative to engagement surface 42, such as, for example, transverse, perpendicular and/or other angular orientations such as acute or obtuse, co-axial and/or may be offset or staggered.

Extension 48a includes a slot 58a and extension 48b includes a slot 58b. Slots 58a, 58b each extend transverse to engagement surface 42. In some embodiments, slot 58a extends parallel to slot 58b. In some embodiments, slots 58a, 58b each extend parallel to ramp 56a and/or ramp 56b. Due to the curvature of endplate 22 along arc X, slot 58b has a maximum length that is greater than a maximum length of slot 58a, which allows engagement surface 42 to remain parallel to the engagement surface of endplate 24 as implant 20 moves between the unexpanded configuration and the expanded configuration, as discussed herein. Slots 58a, 58b each have an oblong configuration. In some embodiments, slot 58a and/or slot 58b can be variously shaped, such as, for example, oval, triangular, square, polygonal, irregular, uniform, non-uniform, offset, staggered, undulating, arcuate, variable and/or tapered. In some embodiments, slot 58a and/or slot 58b may be disposed at alternate orientations, relative to engagement surface 42, ramp 56a and/or ramp 56b, such as, for example, transverse, perpendicular and/or other angular orientations such as acute or obtuse, co-axial and/or may be offset or staggered.

Extension 50 includes a planar portion 60 and a ramp 62 that extends from planar portion 60. Ramp 62 is configured to slidably engage inclined portions of wedge 26 to move implant 20 between the unexpanded configuration shown in FIGS. 1 and 3 and the expanded configuration shown in FIGS. 2 and 4, as discussed herein. Planar portion 60 extends parallel to engagement surface 42, planar portion 54a and/or planar portion 54b. Ramp 62 extends parallel to ramp 56a and/or ramp 56b. In some embodiments, planar portion 60 extends parallel to engagement surface 42 and ramp 62 extends transverse to engagement surface 42. In some embodiments, ramp 62 extends at an acute angle relative to engagement surface 42. In some embodiments, planar portion 60 and/or ramp 62 may be disposed at alternate orientations, relative to engagement surface 42, planar portion 54a, planar portion 54b, ramp 56a and/or ramp 56b, such as, for example, transverse, perpendicular and/or other angular orientations such as acute or obtuse, co-axial and/or may be offset or staggered.

Figure 7:
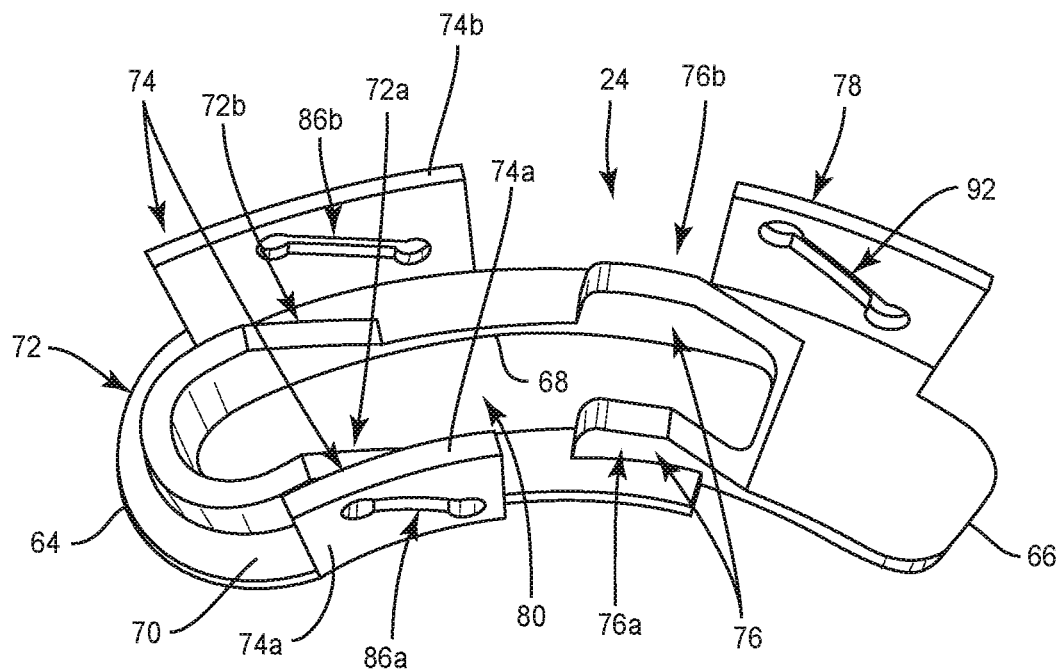
FIG. 7 is a top, perspective view of a component of the implant shown in FIG. 1.
Figure 8:
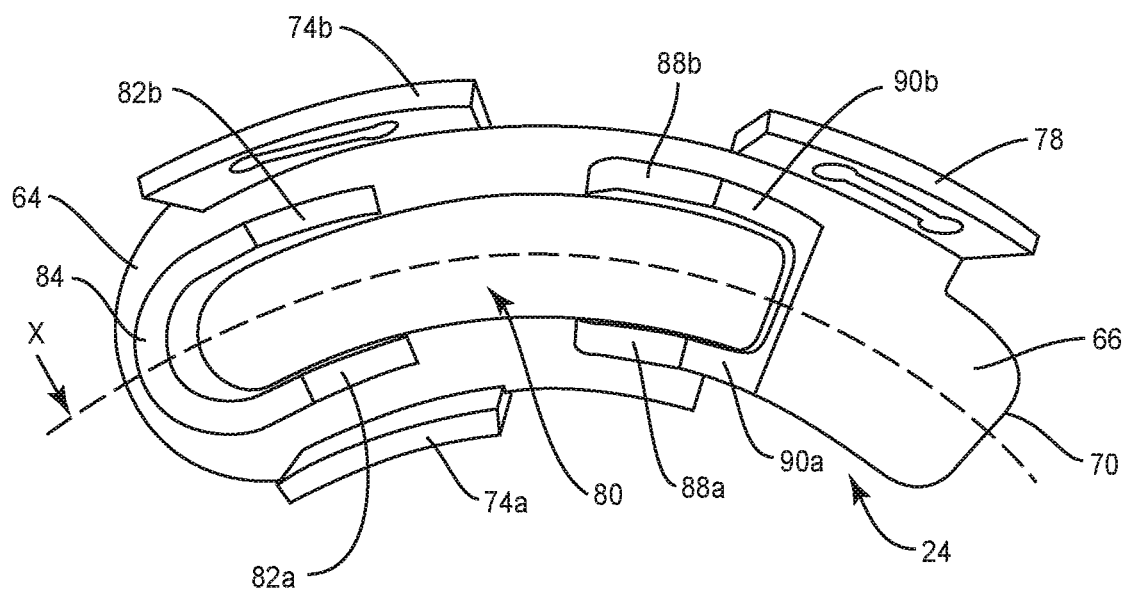
FIG. 8 is a top view of a component of the implant shown in FIG. 1.

Endplate 24 extends along arc X between an end 64 and an opposite end 66, as shown in FIGS. 7 and 8. End 64 is positioned adjacent to end 30 of implant 20 and end 66 is positioned adjacent to end 32 of implant 20. Endplate 24 is curved along arc X. As such, one side of endplate 24 is convexly curved between ends 64, 66 and an opposite side of endplate 24 is concavely curved between ends 64, 66. Endplate 24 comprises an engagement surface 68 configured to engage a second vertebra and an inner surface 70 opposite engagement surface 68. Inner surface 70 faces away from engagement surface 68. Endplate 24 comprises extensions 72, 74, 76, 78 that extend from inner surface 70 such that extensions 72, 74, 76, 78 each extend away from engagement surface 68. Extension 72 includes an extension 72a and an extension 72b that is spaced apart from extension 72a by an opening 80 that extends through engagement surface 68 and inner surface 70. Extension 74 includes an extension 74a and an extension 74b that is spaced apart from extension 74a such that extensions 72a, 72b are positioned between extensions 74a, 74b. Extension 76 includes an extension 76a and an extension 76b that is spaced apart from extension 76a by opening 80. Extension 78 is positioned adjacent to extension 76 such that extension 76b is positioned between extension 76a and extension 78.

Extension 72a includes a ramp 82a and extension 72b includes a ramp 82b that is joined to ramp 82a by a planar portion 84 of extension 72. Ramps 82a, 82b are configured to slidably engage inclined portions of wedge 26 to move implant 20 between the unexpanded configuration shown in FIGS. 1 and 3 and the expanded configuration shown in FIGS. 2 and 4, as discussed herein. Planar portion 84 extends parallel to engagement surface 68. Ramp 82a extends parallel to ramp 82b. In some embodiments, planar portion 84 extends parallel to engagement surface 68 and ramps 82a, 82b each extend transverse to engagement surface 68. In some embodiments, ramps 82a, 82b extend at an acute angle relative to engagement surface 68. In that endplate 24 is curved along arc X, ramp 82b has a maximum length that is greater than a maximum length of ramp 82a. This allows engagement surface 68 to remain parallel to engagement surface 42 of endplate 22 as implant 20 moves between the unexpanded configuration and the expanded configuration, as discussed herein. In some embodiments, planar portion 84, ramp 82a and/or ramp 82b may be disposed at alternate orientations, relative to engagement surface 68, such as, for example, transverse, perpendicular and/or other angular orientations such as acute or obtuse, co-axial and/or may be offset or staggered.

Extension 74a includes a slot 86a and extension 74b includes a slot 86b. Slots 86a, 86b each extend transverse to engagement surface 68. In some embodiments, slot 86a extends parallel to slot 86b. In some embodiments, slots 86a, 86b each extend parallel to ramp 82a and/or ramp 82b. Due to the curvature of endplate 24 along arc X, slot 86b has a maximum length that is greater than a maximum length of slot 86a, which allows engagement surface 68 to remain parallel to engagement surface 42 of endplate 22 as implant 20 moves between the unexpanded configuration and the expanded configuration, as discussed herein. Slots 86a, 86b each have an oblong configuration. In some embodiments, slot 86a and/or slot 86b can be variously shaped, such as, for example, oval, triangular, square, polygonal, irregular, uniform, non-uniform, offset, staggered, undulating, arcuate, variable and/or tapered. In some embodiments, slot 86a and/or slot 86b may be disposed at alternate orientations, relative to engagement surface 68, ramp 82a and/or ramp 82b, such as, for example, transverse, perpendicular and/or other angular orientations such as acute or obtuse, co-axial and/or may be offset or staggered.

Extension 76a includes a planar portion 88a and a ramp 90a that extends from planar portion 88a, Extension 76b includes a planar portion 88b and a ramp 90b that extends from planar portion 88b. Ramps 90a, 90b are configured to slidably engage inclined portions of wedge 26 to move implant 20 between the unexpanded configuration shown in FIGS. 1 and 3 and the expanded configuration shown in FIGS. 2 and 4, as discussed herein. Planar portion 88a extends parallel to planar portion 88b. Ramp 90a extends parallel to ramp 90b. In some embodiments, planar portions 88a, 88b each extend parallel to engagement surface 68 and ramps 90a, 90b each extend transverse to engagement surface 68. In some embodiments, ramps 90a, 90b extend at an acute angle relative to engagement surface 68. In that endplate 24 is curved along arc X, planar portion 88b has a maximum length that is greater than a maximum length of planar portion 88a and ramp 90b has a maximum length that is greater than a maximum length of ramp 90a. This allows engagement surface 68 to remain parallel to engagement surface 42 of endplate 22 as implant 20 moves between the unexpanded configuration and the expanded configuration, as discussed herein. In some embodiments, ramp 90a and/or ramp 90b extends parallel to ramp 82a and/or ramp 82b. In some embodiments, planar portion 88a, planar portion 88b, ramp 90a and/or ramp 90b may be disposed at alternate orientations, relative to engagement surface 68, such as, for example, transverse, perpendicular and/or other angular orientations such as acute or obtuse, co-axial and/or may be offset or staggered.

Extension 78 includes a slot 92 that extends transverse to engagement surface 68. In some embodiments, slot 92 extends parallel to ramp 90a and/or ramp 90b. Slot 92 has an oblong configuration. In some embodiments, slot 92 can be variously shaped, such as, for example, oval, triangular, square, polygonal, irregular, uniform, non-uniform, offset, staggered, undulating, arcuate, variable and/or tapered. In some embodiments, slot 92 extends parallel to slot 86a and/or slot 86b. In some embodiments, slot 92 may be disposed at alternate orientations, relative to engagement surface 68, ramp 90a and/or ramp 90b, such as, for example, transverse, perpendicular and/or other angular orientations such as acute or obtuse, co-axial and/or may be offset or staggered.

Figure 9:
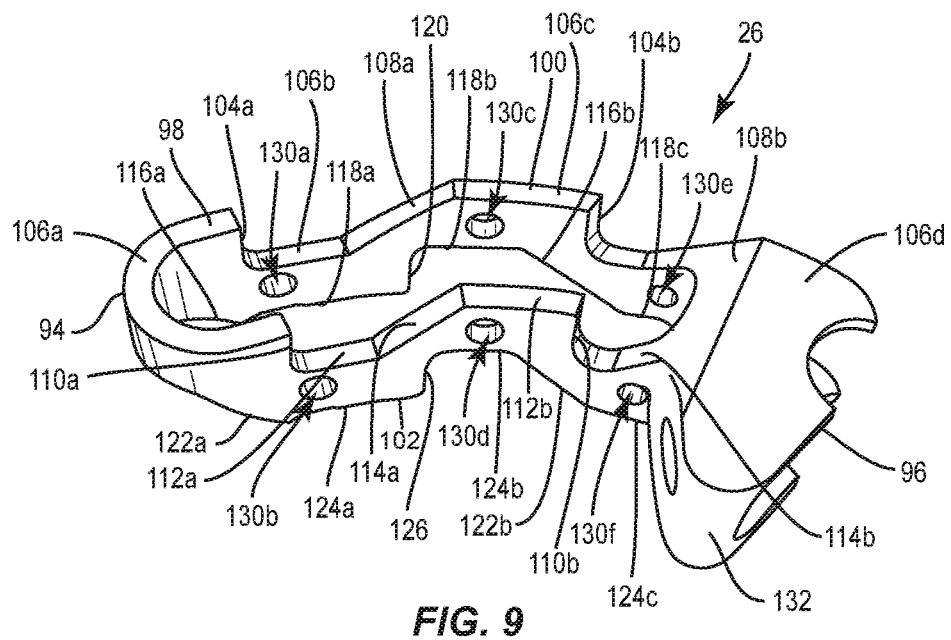
FIG. 9 is a top, perspective view of a component of the implant shown in FIG. 1.
Figure 10:
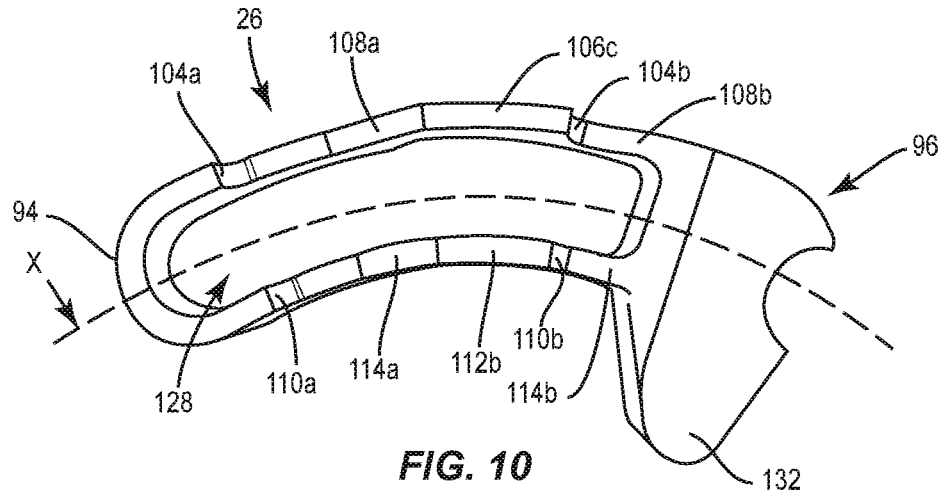
FIG. 10 is a top view of a component of the implant shown in FIG. 1.

Wedge 26 extends along arc X between an end 94 and an opposite end 96, as shown in FIGS. 9 and 10. End 94 is positioned adjacent to end 30 of implant 20 and end 96 is positioned adjacent to end 32 of implant 20, Wedge 26 is curved along arc X. As such, one side of wedge 26 is convexly curved between ends 94, 96 and an opposite side of wedge 26 is concavely curved between ends 94, 96. Wedge 26 includes a wall 98 having an upper surface 100 and a lower surface 102 opposite upper surface 100.

Upper surface 100 includes spaced apart vertical portions 104a, 104b, horizontal portions 106a, 106b, 106c, 106d and inclined portions 108a, 108b. Vertical portion 104a is positioned between horizontal portion 106a and horizontal portion 106b. Inclined portion 108a is positioned between horizontal portion 106b and horizontal portion 106c. Inclined portion 108b is positioned between vertical portion 104b and horizontal portion 106d. Inclined portion 108a is configured to slidably engage ramp 56b and inclined portion 108b is configured to slidably engage ramp 62 as implant 20 moves between the unexpanded configuration and the expanded configuration, as discussed herein. Vertical portions 104a, 104b extend parallel to one another. Horizontal portions 106a, 106b, 106c, 106d extend parallel to one another. Horizontal portions 106a, 106b, 106c, 106d extend transverse to vertical portions 104a, 104b. In some embodiments, horizontal portions 106a, 106b, 106c. 106d extend perpendicular to vertical portions 104a, 104b, Inclined portions 108a, 108b each extend transverse to vertical portions 104a, 104b and transverse to horizontal portions 106a, 106b, 106c, 106d. In some embodiments, inclined portions 108a, 108b extend parallel to one another. In some embodiments, inclined portion 108a extends transverse to inclined portion 108b.

Upper surface 100 includes spaced apart vertical portions 110a, 110b, horizontal portions 112a, 112b and inclined portions 114a, 114b. Vertical portion 110a is positioned between horizontal portion 106a and horizontal portion 112a. Inclined portion 114a is positioned between horizontal portion 112a and horizontal portion 112b. Inclined portion 114b is positioned between vertical portion 110b and horizontal portion 106d. Inclined portion 114a is configured to slidably engage ramp 56a and inclined portion 114b is configured to slidably engage ramp 62 as implant 20 moves between the unexpanded configuration and the expanded configuration, as discussed herein. Vertical portions 110a, 110b extend parallel to one another. In some embodiments, vertical portions 110a, 110b extend parallel to vertical portions 104a, 104b. Horizontal portions 112a, 112b extend parallel to one another. In some embodiments, horizontal portions 112a, 112b extend parallel to horizontal portions 106a, 106b, 106c, 106d. Horizontal portions 112a, 112b extend transverse to vertical portions 110a, 110b. In some embodiments, horizontal portions 112a, 112b extend perpendicular to vertical portions 110a, 110b. Inclined portions 114a, 114b each extend transverse to vertical portions 110a, 110b and transverse to horizontal portions 112a, 112b. In some embodiments, inclined portion 114a extends parallel to inclined portion 108a and inclined portion 114b extends parallel to inclined portion 108b. In some embodiments, inclined portions 114a, 114b extend parallel to one another. In some embodiments, inclined portion 114a extends transverse to inclined portion 114b.

In that wedge 26 is curved along arc X, inclined portion 108a has a maximum length that is greater than a maximum length of inclined portion 114a and inclined portion 108b has a maximum length that is greater than a maximum length of inclined portion 114b. Likewise, horizontal portion 106b has a maximum length that is greater than a maximum length of horizontal portion 112a and horizontal portion 106c has a maximum length that is greater than a maximum length of horizontal portion 112b. This allows engagement surface 68 to remain parallel to engagement surface 42 of endplate 22 as implant 20 moves between the unexpanded configuration and the expanded configuration, as discussed herein.

Lower surface 102 includes spaced apart inclined portions 116a, 116b, horizontal portions 118a, 118b, 118c and a vertical portion 120. Horizontal portion 118a is positioned between inclined portion 116a and vertical portion 120. Horizontal portion 118b is positioned between vertical portion 120 and inclined portion 116b. Inclined portion 116b is positioned between horizontal portion 118b and horizontal portion 118c. Inclined portion 116a is configured to slidably engage ramp 82b and inclined portion 116b is configured to slidably engage ramp 90b as implant 20 moves between the unexpanded configuration and the expanded configuration, as discussed herein. Vertical portion 120 extends parallel to vertical portions 104a, 104b and/or vertical portions 110a, 110b. Horizontal portions 118a, 118b, 118c extend parallel to one another. In some embodiments, horizontal portions 118a, 118b, 118c extend parallel to horizontal portions 106a, 106b, 106c, 106d and/or horizontal portions 112a, 112b. Horizontal portions 118a, 118b, 118c extend transverse to vertical portion 120. In some embodiments, horizontal portions 118a, 118b, 118c extend perpendicular to vertical portion 120. Inclined portions 116a, 116b each extend transverse to vertical portion 120 and transverse to horizontal portions 118a, 118b, 118c. In some embodiments, inclined portions 116a, 116b extend parallel to one another. In some embodiments, inclined portion 116a extends transverse to inclined portion 116b.

Lower surface 102 includes spaced apart inclined portions 122a, 122b, horizontal portions 124a, 124b, 124c and a vertical portion 126. Horizontal portion 124a is positioned between inclined portion 122a and vertical portion 126. Horizontal portion 124b is positioned between vertical portion 126 and inclined portion 122b. Inclined portion 122b is positioned between horizontal portion 124b and horizontal portion 124c. Inclined portion 122a is configured to slidably engage ramp 82a and inclined portion 122b is configured to slidably engage ramp 90a as implant 20 moves between the unexpanded configuration and the expanded configuration, as discussed herein. Vertical portion 126 extends parallel to vertical portion 120, vertical portions 104a, 104b and/or vertical portions 110a, 110b. Horizontal portions 124a, 124b, 124c extend parallel to one another. In some embodiments, horizontal portions 124a, 124b, 124c extend parallel to horizontal portions 118a, 118b, 118c, horizontal portions 106a, 106b, 106c, 106d and/or horizontal portions 112a, 112b. Horizontal portions 124a, 124b, 124c extend transverse to vertical portion 126. In some embodiments, horizontal portions 124a, 124b, 124c extend perpendicular to vertical portion 126. Inclined portions 122a, 122b each extend transverse to vertical portion 126 and transverse to horizontal portions 124a, 124b, 124c. In some embodiments, inclined portions 122a, 122b extend parallel to one another. In some embodiments, inclined portion 122a extends transverse to inclined portion 122b. In some embodiments, inclined portion 122a extends parallel to inclined portion 116a and inclined portion 122b extends parallel to inclined portion 116b.

In that wedge 26 is curved along arc X, inclined portion 116a has a maximum length that is greater than a maximum length of inclined portion 122a and inclined portion 116b has a maximum length that is greater than a maximum length of inclined portion 122b. Likewise, horizontal portion 118b has a maximum length that is greater than a maximum length of horizontal portion 124b and horizontal portion 118a has a maximum length that is greater than a maximum length of horizontal portion 124a. This allows engagement surface 68 to remain parallel to engagement surface 42 of endplate 22 as implant 20 moves between the unexpanded configuration and the expanded configuration, as discussed herein.

Wedge 26 includes a cavity 128. When implant 20 is assembled, cavity 128 is in communication with openings 52, 80 such that a material, such as, for example, bone graft material, can be inserted through opening 52 and/or opening 80 and into cavity 128. Cavity 128 separates horizontal portion 106b from horizontal portion 112a, inclined portion 108a from inclined portion 114a, horizontal portion 106c from horizontal portion 112b, vertical portion 104a from vertical portion 110a, vertical portion 104b from vertical portion 110b and inclined portion 108b from inclined portion 114b. Cavity 128 also separates inclined portion 116a from inclined portion 122a, horizontal portion 118a from horizontal portion 124a, vertical portion 120 from vertical portion 126, horizontal portion 118b from horizontal portion 124b, inclined portion 116b from inclined portion 122b and horizontal portion 118c from horizontal portion 124c.

Wedge 26 comprises a plurality of apertures that extend through wall 98. For example, wedge 26 comprises an aperture 130a that extends through wall 98 between horizontal portions 106b, 118a; an aperture 130b that extends through wall 98 between horizontal portions 112a, 124a; an aperture 130c that extends through wall 98 between horizontal portions 106c, 118b; an aperture 130d that extends through wall 98 between horizontal portions 112b, 124b, an aperture 130e that extends through wall 98 between inclined portion 108b and horizontal portion 118c; and an aperture 130f that extends through wall 98 between inclined portion 114b and horizontal portion 124c. Aperture 130a is coaxial with aperture 130b; aperture 130c is coaxial with aperture 130d; and aperture 130e is coaxial with aperture 130f. Upon assembly of implant 20, apertures 130a, 130b are aligned with slots 86a, 86b of endplate 24 such that a pin extends through apertures 130a, 130b and slots 86a, 86b, as discussed herein; apertures 130c, 130d are aligned with slots 58a, 58b of endplate 22 such that a pin extends through apertures 130c, 130d and slots 58a, 58b, as discussed herein;

and apertures 130e, 130f are aligned with slot 92 of endplate 24 such that a pin extends through apertures 130e, 130f and slot 92, as discussed herein.

Figure 10A:
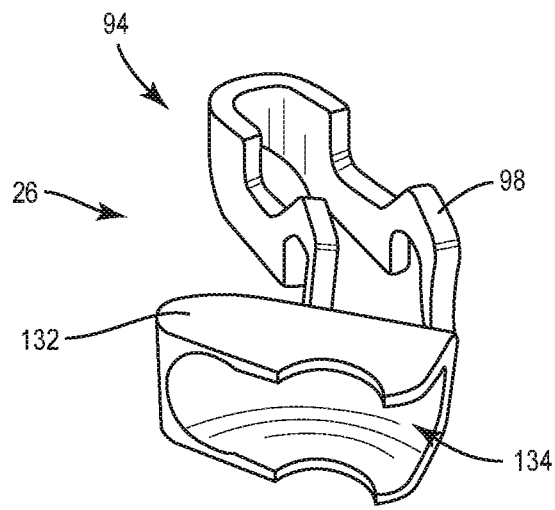
FIG. 10A is an end, perspective view of a component of the implant shown in FIG. 1.

End 96 of wedge 26 comprises an enlarged end wall 132, as shown in FIG. 10A. Wall 132 has a maximum width that is greater than a maximum width of end 94 and/or wall 98. An inner surface of wall 132 defines an arcuate trough 134. Trough 134 is configured for disposal of an actuator of implant 20, as discussed herein. In some embodiments trough 134 has a continuous radius of curvature from a first end of trough 134 to a second end of trough 134. In some embodiments trough 134 has a variable radius of curvature from the first end of trough 134 to the second end of trough 134.

Figure 11:
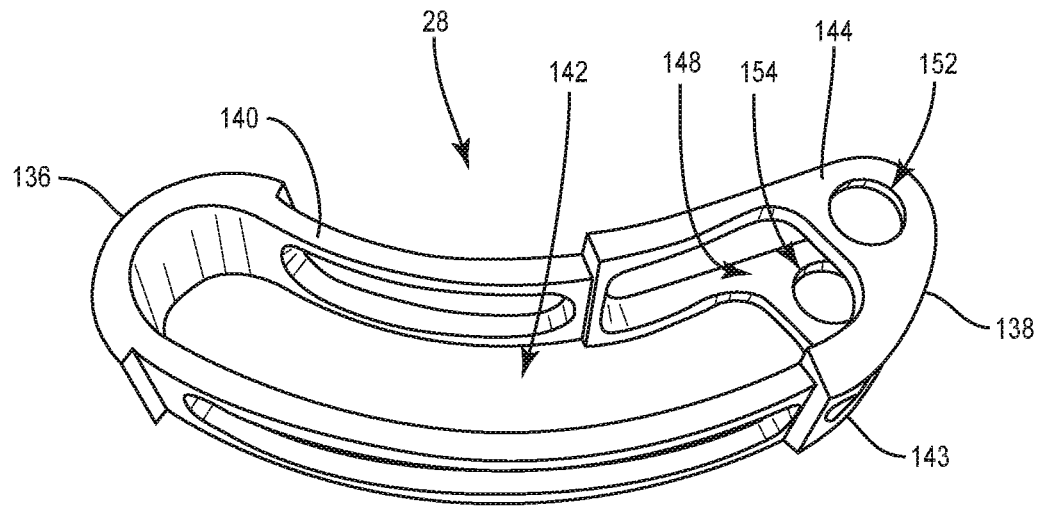
FIG. 11 is a top, perspective view of a component of the implant shown in FIG. 1.
Figure 12:
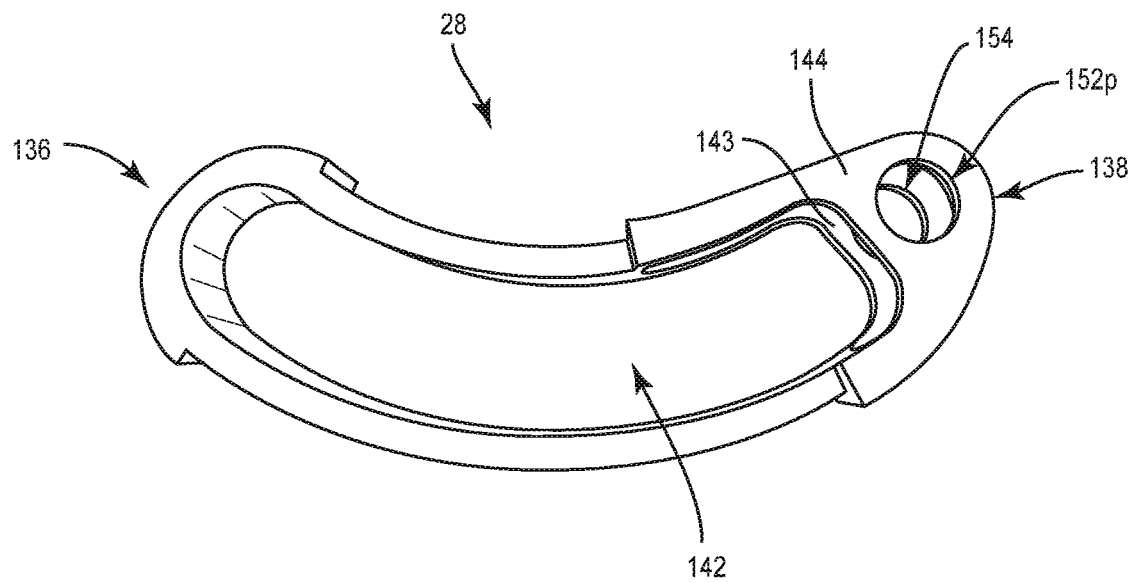
FIG. 12 is a top view of a component of the implant shown in FIG. 1.

Frame 28 extends between an end 136 and an opposite end 138, as shown in FIGS. 11 and 12. End 136 is positioned adjacent to end 30 of implant 20 and end 138 is positioned adjacent to end 32 of implant 20. Frame 28 is curved along arc X between end 136 and end 138. Frame 28 includes a wall 140 having an inner surface that defines an interior cavity 142. Wedge 26 and at least a portion of each of endplates 22, 24 are positioned within interior cavity 142. End 138 of frame 28 includes an upper wall 143 and a lower wall 144. Upper wall 143 is spaced apart from lower wall 144 to define a recess 148 between upper wall 143 and lower wall 144. Recess 148 is configured for disposal of a pivot 150, as discussed herein. Upper wall 143 includes an opening 152 that is aligned with an opening 154 in lower wall 144. Openings 152, 154 are each configured for disposal of a pivot plug to couple pivot 150 to frame 28, as discussed herein. In some embodiments, opening 152 is coaxial with opening 154.

Figure 13:
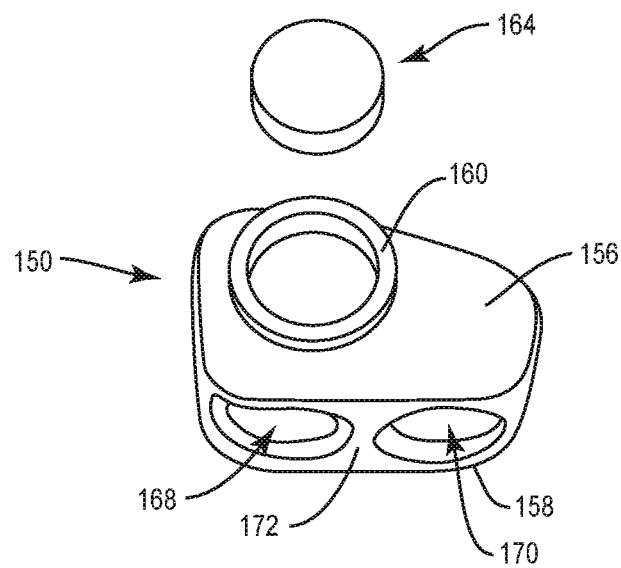
FIG. 13 is a top, perspective view of a component of the implant shown in FIG. 1.
Figure 14:
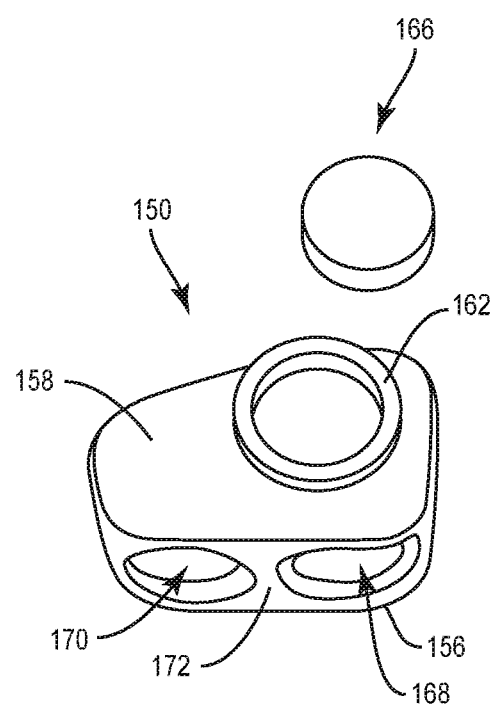
FIG. 14 is a bottom, perspective view of a component of the implant shown in FIG. 1.

Pivot 150 includes an upper surface 156 and a lower surface 158 opposite upper surface 156, as shown in FIGS. 13 and 14. Pivot 150 includes a ring 160 that extends from upper surface 156 and a ring 162 that extends from lower surface 158. Rings 160, 162 are aligned with one another such that ring 160 is coaxial with ring 162. Rings 160, 162 each have an inner diameter that is equivalent to opening 152 and/or opening 154. When pivot 150 is positioned within recess 148, ring 160 is aligned with opening 152 such that a plug, such as, for example, a pivot plug 164 extends through opening 152 and into ring 160, and ring 162 is aligned with opening 154 such that a plug, such as, for example, a pivot plug 166 extends through opening 154 and into ring 162 to couple pivot 150 to frame 28, as discussed herein.

Figure 15:
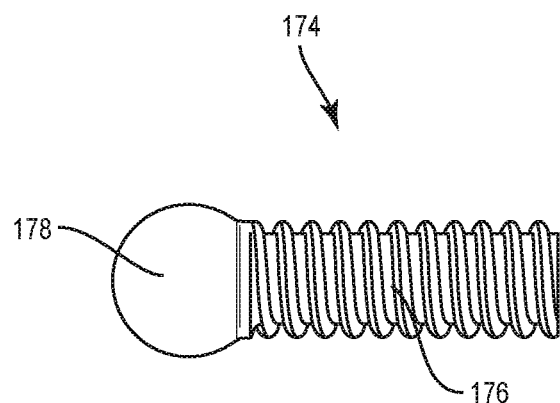
FIG. 15 is a side view of a component of the implant shown in FIG. 1.

Pivot 150 includes a threaded passageway 168 and a threaded passageway 170 that are spaced apart from passageway 168 by a wall 172. Passageways 168, 170 are each configured for disposal of an insertion tool and/or an actuator 174 of implant 20. The insertion tool may be used to insert implant 20 between adjacent vertebrae, for example. Actuator 174 includes a threaded shaft 176 and a ball-shaped tip 178 attached to shaft 176, as shown in FIG. 15, for example. Tip 178 is positioned within trough 134 of wedge 26 and shaft 176 is positioned within passageway 168 or passageway 170 such that the threads on shaft 176 engage threads of passageway 168 or threads of passageway 170. Rotation of shaft 176 within passageway 168 or passageway 170 causes actuator 174 to translate axially relative to pivot 150 such that tip 178 pushes wedge 26 relative to endplates 22, 24 and frame 28 to move implant 20 from the unexpanded configuration to the expanded configuration, as discussed herein. In some embodiments, shaft 176 includes a socket that is configured to mate with a bit of a driver such that the bit of the driver can be inserted within the socket to rotate actuator 174 relative to pivot 150. In some embodiments, the socket may have a cruciform, Phillips, square, hexagonal, polygonal, star or hexalobe cross sectional configuration. It is envisioned that the socket may have any configuration that allows the tip of the driver to mate with the socket such that rotation of the driver rotates actuator 174.

Through holes and slots could be provided in the components described to allow injection of graft material from outside the interbody device into opening 52, opening 80 and/or cavity 128 to promote fusion. The graft material could be transported from outside the incision into opening 52, opening 80 and/or cavity 128, or could be loaded at some intermediary holding chamber, possibly within the inserter midway into the incision, to then be injected or passed into opening 52, opening 80 and/or cavity 128. One specific example might be providing a loading tube integral to the actuator driver which would then flow into a central hole in actuator 174, then into the common cavity of endplate 22, endplate 24 and wedge 26. It is conceived that the graft material would flow into the common cavity, then ports provided in an outer wall of implant 20 to allow the graft to flow into the interbody space. Anchoring features may also be included to allow flow from outside implant 20 into the disc space directly, bypassing implant 20 altogether.

Figure 16:
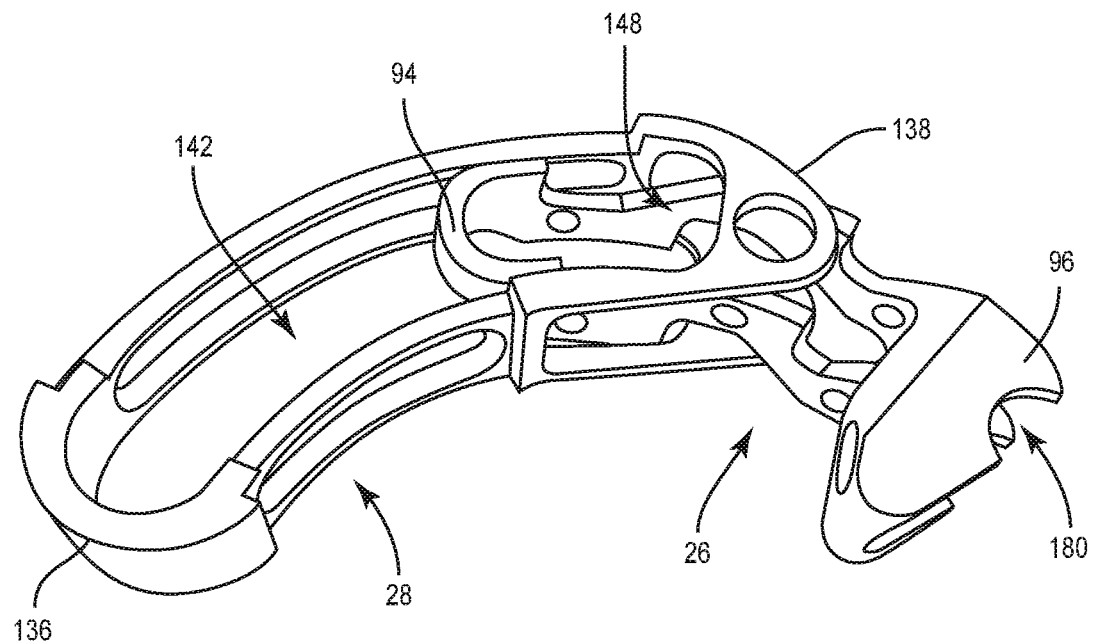
FIG. 16 is a top, perspective view of components of the implant shown in FIG. 1.
Figure 17:
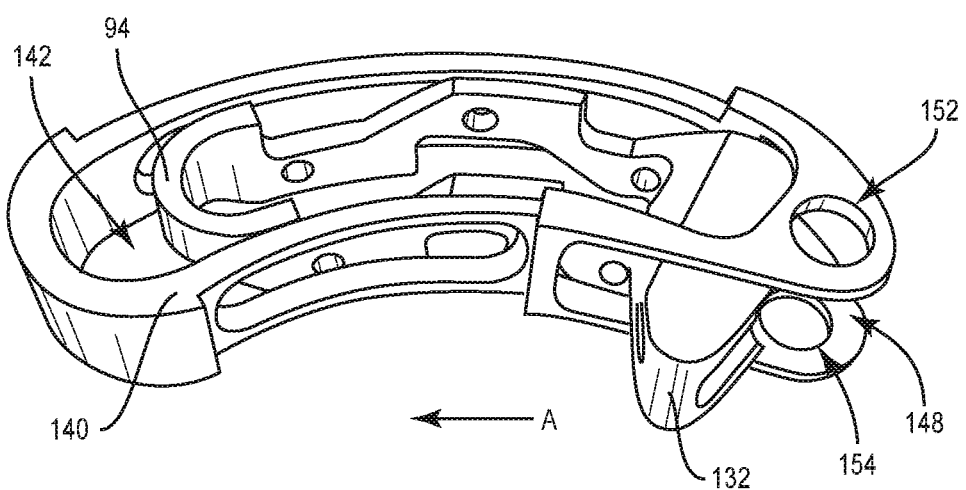
FIG. 17 is a top, perspective view of components of the implant shown in FIG. 1.

Implant 20 may be assembled by positioning wedge 26 through recess 148 of frame 28 such that end 94 of wedge 26 is positioned within cavity 142 of frame 28, as shown in FIG. 16. Wedge 26 is translated relative to frame 28 in the direction shown by arrow A in FIG. 17 such that end 94 of wedge 26 is positioned within cavity 142 of frame 28 and wall 132 of wedge 26 is positioned within recess 148 of frame 28 such that an arcuate cutout 180 of wedge 26 is aligned with openings 152, 154, as shown in FIG. 17. End 94 of wedge 26 is positioned entirely within cavity 142 such that end 94 is surrounded by wall 140 of frame 28.

Figure 18:
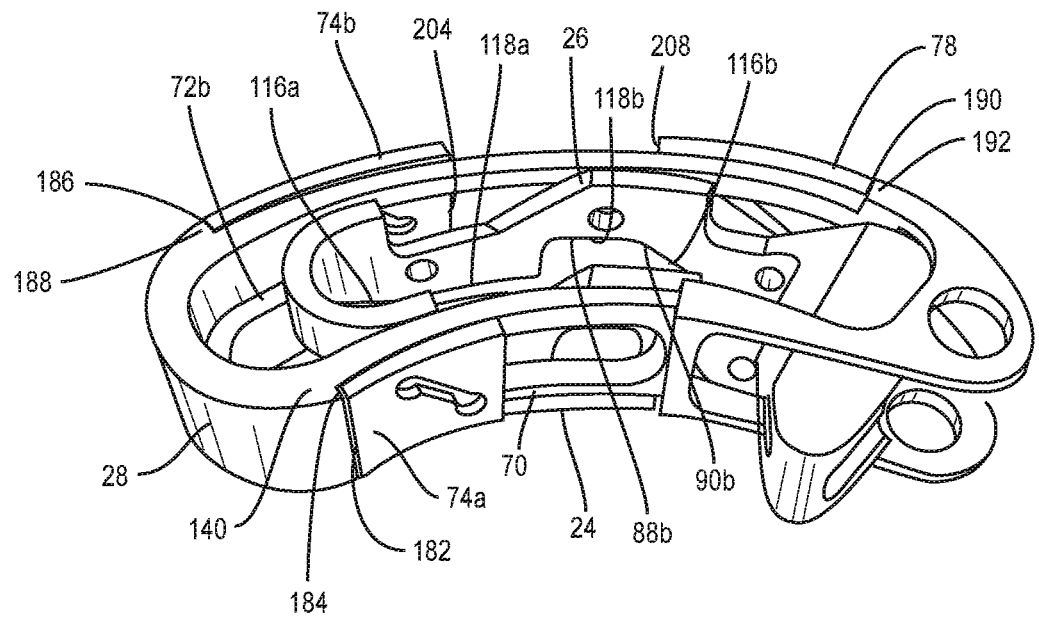
FIG. 18 is a top, perspective view of components of the implant shown in FIG. 1.
Figure 19:
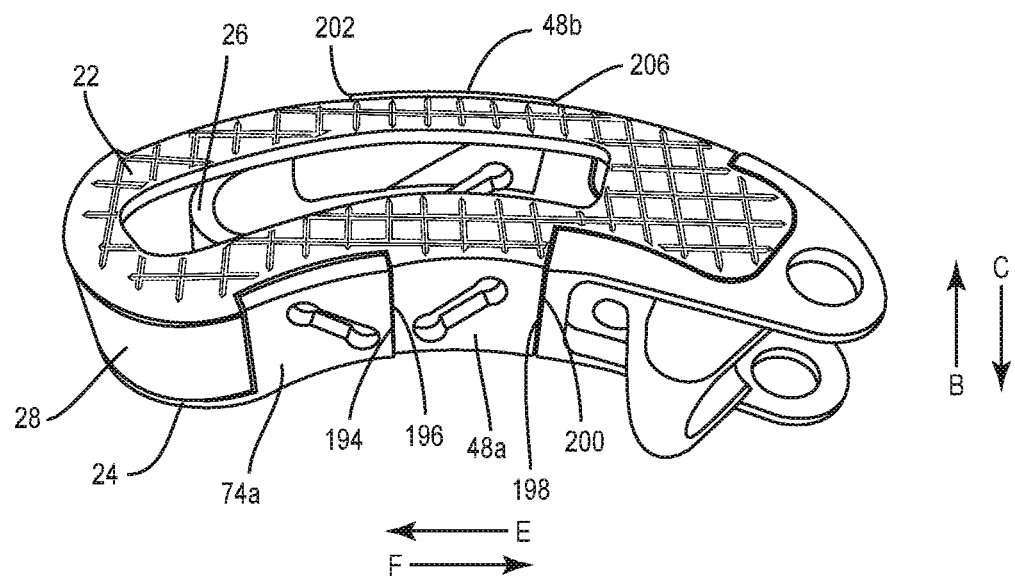
FIG. 19 is a top, perspective view of components of the implant shown in FIG. 1.

Endplate 24 is coupled to frame 28 by positioning wall 140 of frame 28 between extensions 72a, 74a of endplate 24, between extensions 72b, 74b of endplate 24 and between extensions 76b, 78 of endplate 24, as shown in FIG. 18. An axial surface 182 of extension 74a engages a flange 184 of frame 28; an axial surface 186 of extension 74b engages a flange 188 of frame 28; and an axial surface 190 of extension 78 engages a flange 192 of frame 28. Endplate 24 is positioned relative to wedge 26 such that inclined portion 116a of wedge 26 engages ramp 82b of endplate 24, inclined portion 122a of wedge 26 engages ramp 82a of endplate 24, horizontal portions 118a, 124a of wedge 26 engage inner surface 70 of endplate 24, horizontal portion 118b of wedge 26 engages planar portion 88b of endplate 24, horizontal portion 124b of wedge 26 engages planar portion 88a of endplate 24, inclined portion 116b of wedge 26 engages ramp 90b of endplate 24 and inclined portion 122b of wedge 26 engages ramp 90a of endplate 24.

Endplate 22 is coupled to frame 28 by positioning wall 140 of frame 28 between extensions 46a, 48a of endplate 22 and between extensions 46b, 48b of endplate 22. Endplate 22 is positioned relative to endplate 24 such that an axial surface 194 of extension 48a engages an axial surface 196 of extension 74a and an opposite axial surface 198 of extension 48a engages a flange 200 of frame 28. Likewise, an axial surface 202 of extension 48b engages an axial surface 204 of extension 74b, and an opposite axial surface 206 of extension 48b engages a flange 208 of frame 28. The configuration and engagement of axial surfaces 182, 186, 190, 194, 196, 202, 204, 206 and flanges 184, 188, 192, 200, 208 keys endplates 22, 24 with frame 28 such that endplate 22 moves relative to frame 28 in the direction shown by arrow B in FIG. 19 and endplate 24 moves relative to frame 28 in the direction shown by arrow C in FIG. 19 as implant 20 moves from the unexpanded configuration to the expanded configuration, as discussed herein, Endplate 22 is coupled to wedge 26 such that planar portion 54a of endplate 22 engages horizontal portion 112a, planar portion 54b of endplate 22 engages horizontal portion 106b of wedge 26, ramp 56a of endplate 22 engages inclined portion 108a of wedge 26, ramp 56b of endplate 22 engages inclined portion 114a of wedge 26 and ramp 62 of endplate 22 engages inclined portions 108b, 114b of wedge 26.

Figure 20:
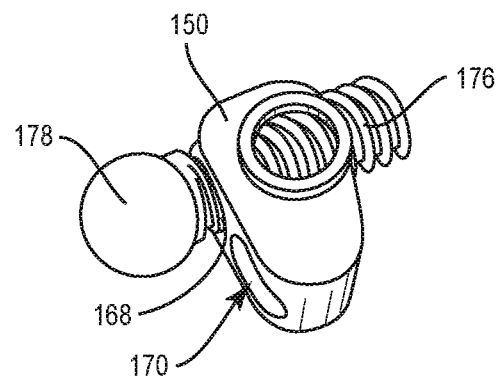
FIG. 20 is a top, perspective view of components of the implant shown in FIG. 1.
Figure 21:
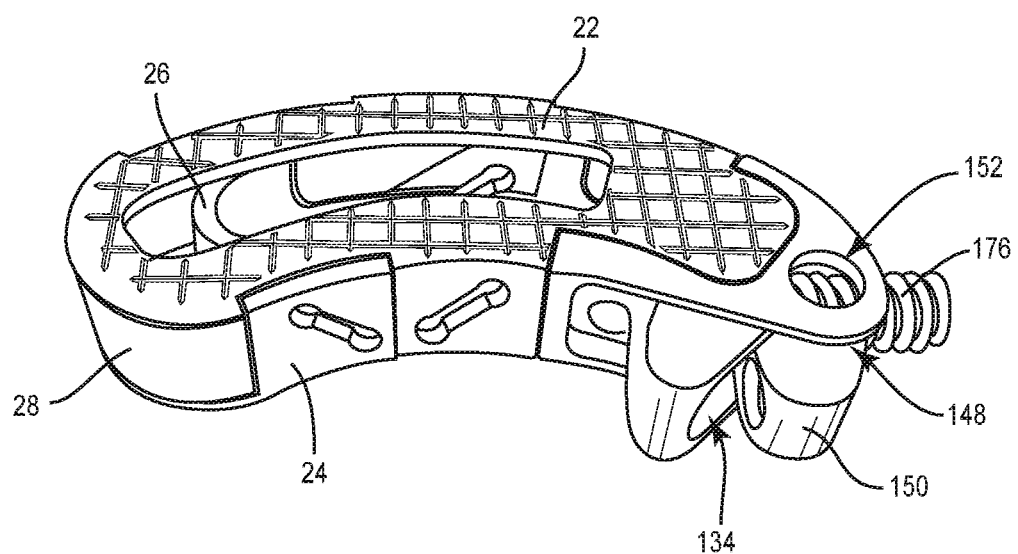
FIG. 21 is a top, perspective view of components of the implant shown in FIG. 1.

Actuator 174 is coupled to pivot 150 by inserting shaft 176 of actuator 174 into one of passageways 168, 170 such that threads on shaft 176 engage the threads of one of passageways 168, 170, as shown in FIG. 20. Tip 178 of actuator 174 is positioned within trough 134 of wedge 26 and pivot 150 is positioned within recess 148 of frame 28 such that ring 160 of pivot 150 is aligned with opening 152 of frame 28, and ring 162 of pivot 150 is aligned with opening 154 of frame 28, as shown in FIG. 21.

Figure 22:
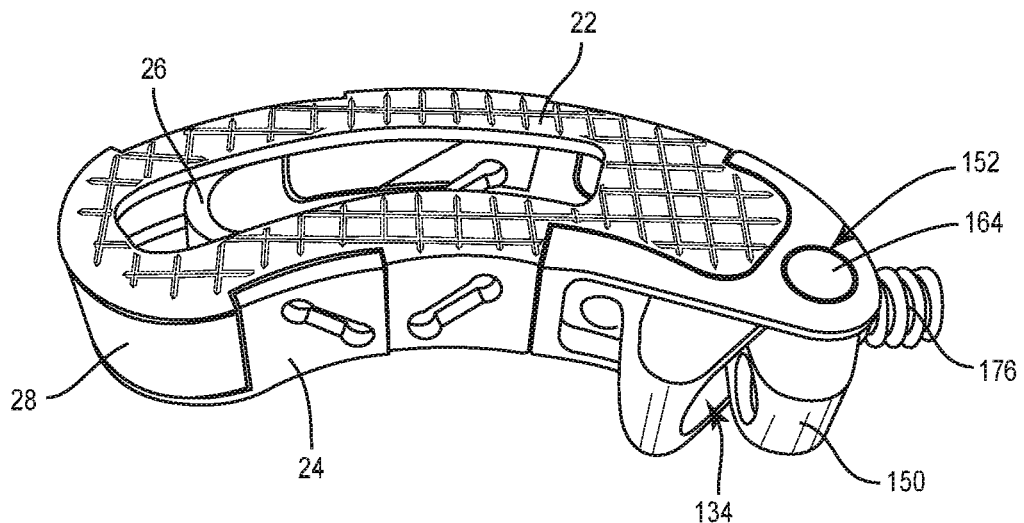
FIG. 22 is a top, perspective view of components of the implant shown in FIG. 1.
Figure 23:
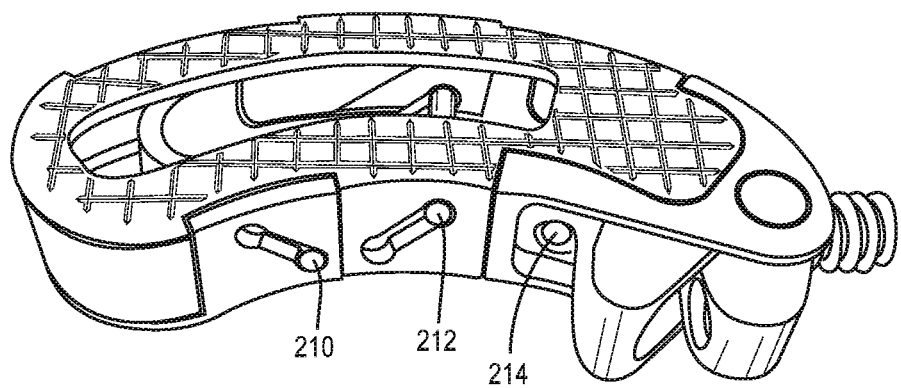
FIG. 23 is a top, perspective view of components of the implant shown in FIG. 1.
Figure 24:
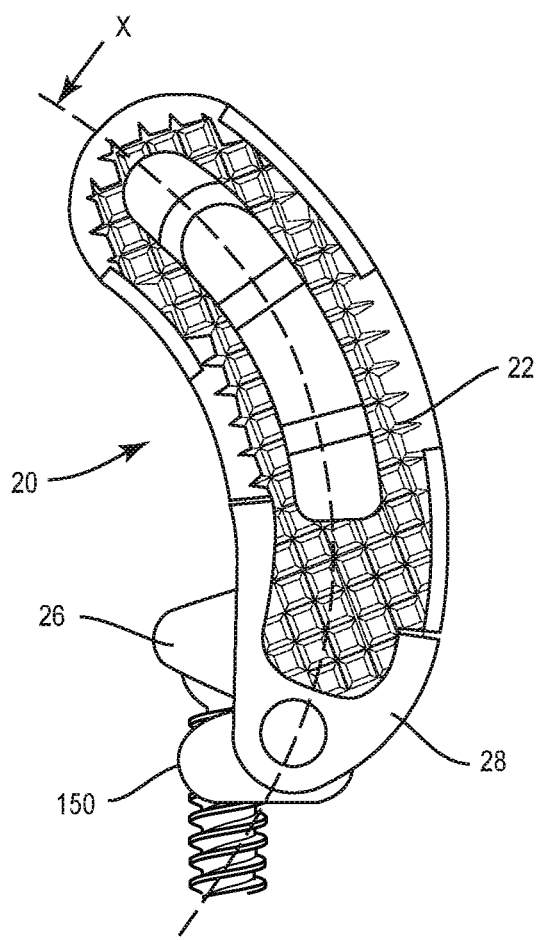
FIG. 24 is a top view of the implant shown in FIG. 1.
Figure 25:
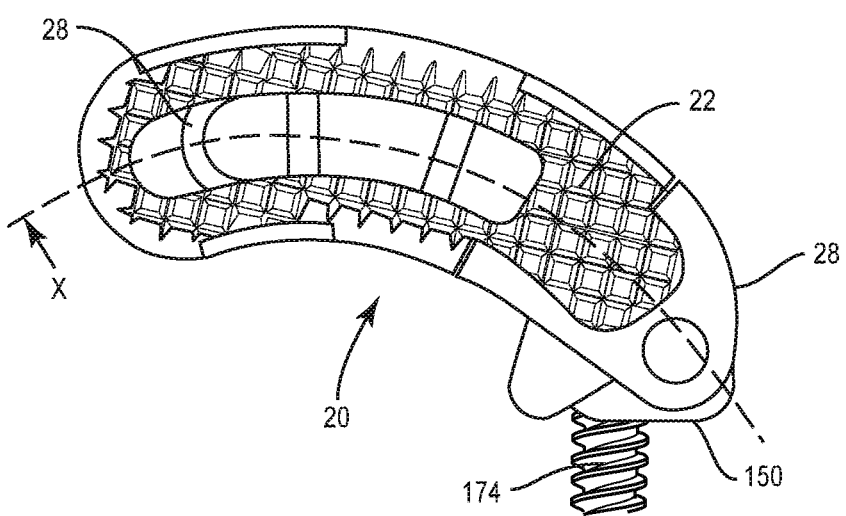
FIG. 25 is a top view of the implant shown in FIG. 1.

As shown in FIG. 22, pivot plug 164 is positioned through opening 152 of frame 28 and into ring 160 of pivot 150 and pivot plug 166 is positioned through opening 154 of frame 28 and into ring 162 of pivot 150 to couple pivot 150 to frame 28 such that pivot 150 is pivotable relative to frame 28 about rings 160, 162 and/or pivot plugs 164, 166. A first pin 210 is positioned through apertures 130a, 130b of wedge 26 and slots 86a, 86b of endplate 24, as shown in FIG. 23. A second pin 212 is positioned through apertures 130c, 130d of wedge 26 and slots 58a, 58b of endplate 22. A third pin 214 is positioned through apertures 130e, 130f of wedge 26 and slot 92 of endplate 24.

In operation and use, the interbody implant system is employed with a surgical procedure, such as, a fusion treatment of a spine of a patient including vertebrae and body areas adjacent thereto, as discussed herein. The interbody implant system may also be employed with other surgical procedures, such as, for example, discectomy, laminotomy, laminectomy, nerve-root retraction, foramenotomy, facetectomy, decompression, and spinal, nucleus or disc replacement.

For example, the interbody implant system can be employed with a surgical arthrodesis procedure, such as, for example, an interbody fusion for treatment of an applicable condition or injury of an affected section of a spinal column and adjacent areas within a body, such as, for example, an intervertebral disc space between a first vertebra and a second vertebra. It is contemplated that intervertebral implant 20 of the interbody implant system, described above, can be inserted within the intervertebral disc space to space apart articular joint surfaces, provide support and maximize stabilization of the vertebrae. It is further contemplated that intervertebral implant 20 provides height restoration between vertebral bodies, decompression, restoration of sagittal balance and/or resistance of subsidence into vertebral endplates.

In use, to treat the affected section of the vertebrae, a medical practitioner obtains access to a surgical site including the vertebrae in any appropriate manner, such as through incision and retraction of tissues. It is envisioned that the interbody implant system can be used in any existing surgical method or technique including open surgery, mini-open surgery, minimally invasive surgery and percutaneous surgical implantation, whereby the vertebrae are accessed through a mini-incision or sleeve that provides a protected passageway to the area. Once access to the surgical site is obtained, the particular surgical procedure is performed for treating the spine disorder. Intervertebral implant 20, described above, is then employed to augment the surgical treatment. Intervertebral implant 20 can be delivered or implanted as a pre-assembled device or can be assembled in situ. Intervertebral implant 20 can be completely or partially revised, removed or replaced in situ. It is contemplated that one or all of the components of the interbody implant system can be delivered to the surgical site via manual manipulation and/or a free hand technique. It is further contemplated that intervertebral implant 20 may be inserted posteriorly, and then manipulated anteriorly and/or lateral and/or medial.

An incision is made in the body of a patient and a cutting instrument creates a surgical pathway for implantation of intervertebral implant 20 within the patient's body. A guide instrument (not shown) is employed to initially distract the first vertebra from the second vertebra. A sleeve or cannula is used to access the intervertebral disc space and facilitate delivery and access for components of the interbody implant system. A preparation instrument can be inserted within the sleeve or cannula and disposed within the intervertebral disc space. The preparation instrument(s) can be employed to remove some or all of the disc tissue including the disc nucleus and fluids, adjacent tissues and/or bone, corticate, scrape and/or remove tissue from the surfaces of endplates of the first and second vertebrae, as well as for aspiration and irrigation of the region according to the requirements of a particular surgical application.

Intervertebral implant 20 is inserted into the patient with implant 20 disposed in the unexpanded configuration shown in FIGS. 1 and 3. Implant 20 is delivered along the surgical pathway using a substantially posterior approach to position implant 20 within the intervertebral disc space. In some embodiments, an end of an inserter is positioned within passageway 168 or passageway 170 of pivot 150 to couple implant 20 with the inserter. In some embodiments, the end of the inserter includes a threaded tip that mates with threads of passageway 168 or passageway 170 of pivot 150 to couple implant 20 with the inserter. The inserter is then manipulated to deliver implant 20 into the prepared intervertebral disc space, between the first vertebra and the second vertebra, according to the requirements of a particular surgical application.

Once implant 20 is positioned within the intervertebral disc space, implant 20 may be moved within the intervertebral disc space such that implant 20 is positioned within the intervertebral disc space at a selected angle by moving pivot 150 such that pivot 150 rotates relative to endplates 22, 24, wedge 26 and frame 28. That is, implant 20 may be rotated within the intervertebral disc space by articulating pivot 150 to rotate pivot 150 relative to endplates 22, 24, wedge 26 and frame 28. In some embodiments, pivot 150 is rotated relative to endplates 22, 24, wedge 26 and frame 28 by manipulating the inserter. For example, the inserter may be used to pivot endplates 22, 24, wedge 26 and frame 28 relative to pivot 150 from a first angle shown in FIG. 24 to a second angle shown in FIG. 25. In some embodiments, the difference between the first and second angles is between about 15 degrees and about 85 degrees. In some embodiments, pivot 150 is articulated relative to endplates 22, 24, wedge 26 and frame 28 such that implant 20 is disposed at a selected angle relative to the inserter before positioning implant 20 within the intervertebral disc space. Implant 20 is then inserted into the intervertebral disc space with implant 20 at the selected angle relative to the inserter to position implant 20 at a selected angle within the intervertebral disc space. Once implant 20 is positioned within the intervertebral disc space with implant 20 at the selected angle, the inserter can be uncoupled from implant 20 by rotating the inserter relative to pivot 150 such that the threaded tip of the inserter backs out of passageway 168 or passageway 170 of pivot 150.

Upon desired positioning of intervertebral implant 20 within the intervertebral disc space, the tip of the driver is inserted into a socket of shaft 176 of actuator 174 to mate features of the tip of the driver with features of the socket of shaft 176 such that rotation of the driver rotates actuator 174 relative to pivot 150. Implant 20 is then deployed within the intervertebral disc space to move implant 20 from the unexpanded configuration, shown in FIGS. 1 and 3, to the expanded configuration, shown in FIGS. 2 and 4. The driver is rotated in a first rotational direction, such as, for example, clockwise or counterclockwise such that actuator 174 moves relative to pivot 150 in the direction shown by arrow D in FIG. 1. As actuator 174 moves in the direction shown by arrow D, tip 178 of actuator 174 pushes against the inner surface of end wall 132 that defines trough 134 of wedge 26 such that wedge 26 moves relative to endplates 22, 24 and frame 28 in the direction shown by arrow D.

As wedge 26 moves relative to endplates 22, 24 and frame 28 in the direction shown by arrow D, ramp 56*a* of endplate 22 slides along inclined portion 108*a* of wedge 26, ramp 56*b* of endplate 22 slides along inclined portion 114*a* of wedge 26, ramp 62 of endplate 22 slides along inclined portions 108*b*, 114*b* of wedge 26, inclined portion 116*a* of wedge 26 slides along ramp 82*b* of endplate 24, inclined portion 122*a* of wedge 26 slides along ramp 82*a* of endplate 24, inclined portion 116*b* of wedge 26 slides along ramp 90*b* of endplate 24 and inclined portion 122*b* of wedge 26 slides along ramp 90*a* of endplate 24. This causes endplate 22 to move relative to frame 28 in the direction shown by arrow B in FIG. 19 and endplate 24 to move relative to frame 28 in the direction shown by arrow C in FIG. 19, which moves implant 20 from the unexpanded configuration to the expanded configuration.

Pin 210 remains positioned within apertures 130*a*, 130*b* of wedge 26 and translates within slots 86*a*, 86*b* of endplate 24 as implant 20 moves from the unexpanded configuration to the expanded configuration. That is, pin 210 moves from one end of each of slots 86*a*, 86*b* to an opposite end of slots 86*a*, 86*b* as implant 20 moves from the unexpanded configuration to the expanded configuration. Pin 212 remains positioned within apertures 130*c*, 130*d* of wedge 26 and translates within slots 58*a*, 58*b* of endplate 22 as implant 20 moves from the unexpanded configuration to the expanded configuration. That is, pin 212 moves from one end of each of slots 58*a*, 58*b* to an opposite end of slots 58*a*, 58*b* as implant 20 moves from the unexpanded configuration to the expanded configuration. Pin 214 remains positioned within apertures 130*e*, 130*f* of wedge 26 and translates within slot 92 of endplate 24 as implant 20 moves from the unexpanded configuration to the expanded configuration. That is, pin 214 moves from one end of slot 92 to an opposite end of slot 92 as implant 20 moves from the unexpanded configuration to the expanded configuration.

Engagement surface 42 of endplate 22 is spaced apart a first distance from engagement surface 68 of endplate 24 when implant 20 is the unexpanded configuration. Engagement surface 42 is spaced apart an increased second distance from engagement surface 68 when implant 20 is in the expanded configuration, shown in FIGS. 2 and 4. In some embodiments, the first distance is about 7 mm and the second distance is at least about 14 mm. In some embodiments, the first distance is about 8 mm and the second distance is at least about 16 mm. In some embodiments, the first distance is about 9 mm and the second distance is at least about 18 mm.

As implant 20 moves from the unexpanded configuration to the expanded configuration, endplate 22 moves away from endplate 24 such that engagement surface 42 of endplate 22 engages the first vertebra and engagement surface 68 of endplate 24 engages the second vertebra. That is, endplate 22 moves relative to frame 28 in the direction shown by arrow B in FIG. 19 and endplate 24 moves relative to frame 28 in the direction shown by arrow C in FIG. 19. As endplates 22, 24 move in the directions shown by arrows B and C, endplate 22 does not translate axially relative to endplate 24 and/or frame 28 and endplate 24 does not translate axially relative to endplate 22 and/or frame 28. That is, endplate 22 does not translate relative to endplate 24 and/or frame 28 in the direction shown by arrow E in FIG. 19 or the direction shown by arrow F in FIG. 19 as endplate 22 moves relative to frame 28 in the direction shown by arrow B in FIG. 19. Likewise, endplate 24 does not translate relative to endplate 22 and/or frame 28 in the direction shown by arrow E in FIG. 19 or the direction shown by arrow F in FIG. 19 as endplate 24 moves relative to frame 28 in the direction shown by arrow C in FIG. 19.

Endplates 22, 24 push against the vertebrae to move the first vertebra away from the second vertebra and to increase the size of the intervertebral disc space. It is contemplated that in the deployed or expanded configuration, intervertebral implant 20 provides height restoration between the first vertebra and the second vertebra, decompression, restoration of sagittal balance and resistance of subsidence into the endplates of the vertebrae. Implant 20 may be kept in the expanded configuration to maintain the increased size of the intervertebral disc space. In some embodiments, a material, such as, for example, bone graft is positioned within cavity 128 of wedge 26 to promote bone growth to fuse the first vertebra with the second vertebra. In some embodiments, the material is inserted through opening 52 of endplate 22 and into cavity 128. In some embodiments, the material is inserted through opening 80 of endplate 24 and into cavity 128. In some embodiments, the material is inserted into cavity 128 through an aperture or other opening in one or more of endplates 22, 24 and frame 28, such as, for example, one or more of slots 58*a*, 58*b*, 86*a*, 86*b*, 92.

In some embodiments, engagement surface 42 extends parallel to engagement surface 68 when implant 20 is in the expanded configuration. In some embodiments, engagement surface 42 extends transverse to engagement surface 68 when implant 20 is in the expanded configuration. It is envisioned that the ramps/inclined portions of endplates 22, 24 and wedge 26 can be configured such that engagement surface 42 extends at any angle between about 0 degrees and about 90 degrees relative to engagement surface 68 when implant 20 is in the expanded configuration.

In one embodiment, the bone graft can be a particulate material, which may include an osteoconductive material such as HA and/or an osteoinductive agent such as a bone morphogenic protein (BMP) to enhance bony fixation of intervertebral implant 20 with the adjacent vertebrae. It is contemplated that the bone graft may include therapeutic polynucleotides or polypeptides. It is further contemplated that the agent and/or bone graft may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. Implant 20 can be made of radiolucent materials such as polymers. Radiomarkers may be included for identification under x-ray, fluoroscopy, CT or other imaging techniques. It is envisioned that the bone graft may include one or a plurality of therapeutic agents and/or pharmacological agents for release, including sustained release, to treat, for example, pain, inflammation and degeneration.

It is envisioned that the components of the interbody implant system, which may include one or a plurality of intervertebral implants 20, can be delivered to the surgical site via alternate approaches. In one embodiment, intervertebral implant 20 is delivered through the surgical pathway along a transforaminal lumbar interbody fusion approach into the intervertebral disc space and disposed in the deployed or expanded configuration. In one embodiment, a plurality of intervertebral implants 20 are delivered through the surgical pathway along a posterior lumbar interbody fusion approach into the intervertebral disc space and disposed in the deployed or expanded configuration in a side by side orientation.

In one embodiment, intervertebral implant 20 can be collapsed from the expanded configuration to an alternate configuration between the expanded configuration and the unexpanded configuration to collapse intervertebral implant 20 as may be desired to reposition with or remove intervertebral implant 20 from the intervertebral disc space. In one embodiment, the interbody implant system includes a plurality of intervertebral implants 20, which can be variously sized and configured, and/or oriented in a side by side engagement, spaced apart and/or staggered.

Implant 20 may be moved from the expanded configuration to the unexpanded configuration by rotating the driver in a second rotational direction, such as, for example, clockwise or counterclockwise such that actuator 174 moves relative to pivot 150 in the direction shown by arrow G in FIG. 1. As actuator 174 moves in the direction shown by arrow G, tip 178 of actuator 174 pulls end wall 132 of wedge 26 in the direction shown by arrow F in FIG. 19 such that wedge 26 moves relative to endplates 22, 24 and frame 28 in the direction shown by arrow F. As wedge 26 moves relative to endplates 22, 24 and frame 28 in the direction shown by arrow F, ramp 56a of endplate 22 slides along inclined portion 108a of wedge 26, ramp 56b of endplate 22 slides along inclined portion 114a of wedge 26, ramp 62 of endplate 22 slides along inclined portions 108b, 114b of wedge 26, inclined portion 116a of wedge 26 slides along ramp 82b of endplate 24, inclined portion 122a of wedge 26 slides along ramp 82a of endplate 24, inclined portion 116b of wedge 26 slides along ramp 90b of endplate 24 and inclined portion 122b of wedge 26 slides along ramp 90a of endplate 24. This causes endplate 22 to move relative to frame 28 in the direction shown by arrow C in FIG. 19 and endplate 24 to move relative to frame 28 in the direction shown by arrow B in FIG. 19, which moves implant 20 from the expanded configuration to the unexpanded configuration.

Pin 210 remains positioned within apertures 130a, 130b of wedge 26 and translates within slots 86a, 86b of endplate 24 as implant 20 moves from the expanded configuration to the unexpanded configuration. That is, pin 210 moves from one end of each of slots 86a, 86b to an opposite end of slots 86a, 86b as implant 20 moves from the expanded configuration to the unexpanded configuration. Pin 212 remains positioned within apertures 130c, 130d of wedge 26 and translates within slots 58a, 58b of endplate 22 as implant 20 moves from the expanded configuration to the unexpanded configuration. That is, pin 212 moves from one end of each of slots 58a, 58b to an opposite end of slots 58a, 58b as implant 20 moves from the expanded configuration to the unexpanded configuration. Pin 214 remains positioned within apertures 130e, 130f of wedge 26 and translates within slot 92 of endplate 24 as implant 20 moves from the expanded configuration to the unexpanded configuration. That is, pin 214 moves from one end of slot 92 to an opposite end of slot 92 as implant 20 moves from the expanded configuration to the unexpanded configuration. Once implant 20 is in the unexpanded configuration implant 20 can be moved within the intervertebral disc space and/or removed from the intervertebral disc space, as desired.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A device to space apart vertebral members, the device comprising:
    a first endplate comprising a first engagement surface and a first ramp;
    a second endplate comprising a second engagement surface and a second ramp;
    a wedge positioned between the endplates, the wedge comprising a first inclined portion that slidably engages the first ramp and a second inclined portion that slidably engages the second ramp;
    a frame having an interior cavity; and
    a pivot coupled to the frame and an actuator that extends through the pivot,
    wherein the wedge is movable relative to the endplates to move the device between a first configuration having a first height between the engagement surfaces and a second configuration having an increased second height between the engagement surfaces,
    wherein the ramps and the wedge being positioned within the interior cavity as the device moves between the first and second configurations, and
    wherein rotation of the actuator relative to the pivot translates the actuator such that the wedge moves relative to the endplates to move the device between the first and second configurations.

2. The device recited in claim 1, further comprising a pin that is positioned in an aperture of the wedge and translates within a slot of one of the endplates as the device moves between the first and second configurations.

3. The device recited in claim 2, wherein the pin is fixed to the wedge as the device moves between the first and second configurations.

4. The device recited in claim 1, further comprising a first pin that is positioned within a first aperture of the wedge and translates within a first slot of the first endplate as the device moves between the first and second configurations and a second pin that is positioned within a second aperture of the wedge and translates within a second slot of the second endplate as the device moves between the first and second configurations.

5. The device recited in claim 4, wherein the pins are fixed to the wedge as the device moves between the first and second configurations.

6. The device recited in claim 1, wherein the first ramp extends transverse to the first engagement surface and the second ramp extends transverse to the second engagement surface.

7. The device recited in claim 1, wherein the first engagement surface extends parallel to the second engagement surface when the device is in the first and second configurations.

8. A device as recited in claim 1, wherein the actuator is a screw having a ball tip, the ball tip being positioned within an arcuate track in the wedge.

9. The device recited in claim 1, wherein the device comprises a cavity that extends through the engagement surfaces and the wedge.

10. The device recited in claim 1, wherein the device is kidney-shaped.

11. The device recited in claim 1, wherein the actuator is a screw.

12. The device recited in claim 1, wherein the actuator is a screw having a ball tip.

13. The device recited in claim 1, wherein the device comprises a cavity that extends through the engagement surfaces.

14. The device recited in claim 1, further comprising a pin that is positioned in the wedge and translates within one of the endplates as the device moves between the first and second configurations.

15. A device to space apart vertebral members, the device comprising:
   a frame having an interior cavity;
   a first endplate comprising a first ramp;
   a second endplate comprising a second ramp;
   a wedge positioned between the endplates, the wedge comprising a first inclined portion that slidably engages the first ramp and a second inclined portion that slidably engages the second ramp; and
   a pivot coupled to the frame and an actuator that extends through the pivot,
   wherein the wedge is movable relative to the endplates to move the device between a first configuration having a first height between the endplates and a second configuration having an increased second height between the endplates, the ramps and the wedge being positioned within the interior cavity as the device moves between the first and second configurations, and
   wherein rotation of the actuator relative to the pivot translates the actuator such that the wedge moves relative to the endplates to move the device between the first and second configurations.

16. The device recited in claim 15, wherein the actuator is a screw having a ball tip, the ball tip being positioned within an arcuate track in the wedge.

17. The device recited in claim 15, further comprising a pin that is positioned in an aperture of the wedge and translates within a slot of one of the endplates as the device moves between the first and second configurations.

18. The device recited in claim 15, further comprising a first pin that is positioned within a first aperture of the wedge and translates within a first slot of the first endplate as the device moves between the first and second configurations and a second pin that is positioned within a second aperture of the wedge and translates within a second slot of the second endplate as the device moves between the first and second configurations.

19. A kidney-shaped device to space apart vertebral members, the device comprising:
   a first endplate comprising a first ramp;
   a second endplate comprising a second ramp;
   a wedge positioned between the endplates, the wedge comprising a first inclined portion that slidably engages the first ramp and a second inclined portion that slidably engages the second ramp; and
   a pin positioned in an aperture of the wedge,
   wherein the device comprises a cavity that extends through the engagement surfaces and the wedge, bone graft being positioned within the cavity, and
   wherein the wedge is movable relative to the endplates to move the device between a first configuration having a first height between the endplates and a second configuration having an increased second height between the endplates, and
   wherein the pin translates within a slot of one of the endplates as the device moves between the first and second configurations.

20. The kidney-shaped device recited in claim 19, wherein the first endplate extends parallel to the second endplate when the device is in the first and second configurations.

* * * * *